United States Patent
Sharma et al.

(10) Patent No.: US 11,335,344 B2
(45) Date of Patent: May 17, 2022

(54) SYSTEM AND METHOD FOR MULTI-MICROPHONE AUTOMATED CLINICAL DOCUMENTATION

(71) Applicant: Nuance Communications, Inc., Burlington, MA (US)

(72) Inventors: Dushyant Sharma, Woburn, MA (US); Patrick A. Naylor, Reading (GB)

(73) Assignee: NUANCE COMMUNICATIONS, INC., Burlington, MA (US)

( * ) Notice: Subject to any disclaimer, the term of this patent is extended or adjusted under 35 U.S.C. 154(b) by 0 days.

(21) Appl. No.: 17/315,916

(22) Filed: May 10, 2021

(65) Prior Publication Data

US 2021/0350809 A1 Nov. 11, 2021

Related U.S. Application Data

(60) Provisional application No. 63/022,269, filed on May 8, 2020.

(51) Int. Cl.
 *G10L 17/06* (2013.01)
 *G10L 15/22* (2006.01)
 (Continued)

(52) U.S. Cl.
 CPC .............. *G10L 15/22* (2013.01); *G06F 16/65* (2019.01); *G06F 16/686* (2019.01); *G06N 20/00* (2019.01);
 (Continued)

(58) Field of Classification Search
 CPC .. G06F 3/03544; G06F 16/686; G06F 16/783; G06F 21/6245; G06F 40/30; G10L 17/06; G10L 21/0232; G10L 25/78; G10L 25/84; G10L 15/08; G10L 25/21; G10L 15/04; G10L 15/187; G10L 15/22; G16H 10/60; G16H 40/20; G16H 15/00;
 (Continued)

(56) References Cited

U.S. PATENT DOCUMENTS 5,930,749 A   7/1999   Maes
6,009,396 A   12/1999  Nagata
(Continued)

FOREIGN PATENT DOCUMENTS

WO   2017220816 A1   12/2017

OTHER PUBLICATIONS

Non-Final Office Action issued in related U.S. Appl. No. 17/315,857 dated Jul. 9, 2021.
(Continued)

*Primary Examiner* — Gerald Gauthier
(74) *Attorney, Agent, or Firm* — Brian J. Colandreo; Michael T. Abramson; Holland & Knight LLP

(57) ABSTRACT

A method, computer program product, and computing system for receiving a plurality of predefined beams associated with a microphone array. A plurality of predefined nulls associated with the microphone array may be received. One or more predefined beams from the plurality of predefined beams or one or more predefined nulls from the plurality of predefined nulls may be selected. A microphone array may obtain audio encounter information, via the microphone array, using at least one of the one or more selected beams and the one or more selected nulls.

6 Claims, 20 Drawing Sheets

(51) Int. Cl.

| | | |
|---|---|---|
| *H04R 1/40* | (2006.01) | |
| *H04R 3/00* | (2006.01) | |
| *G10L 25/84* | (2013.01) | |
| *G10L 15/32* | (2013.01) | |
| *G10L 15/20* | (2006.01) | |
| *G06F 16/65* | (2019.01) | |
| *G06F 16/68* | (2019.01) | |
| *G10L 25/78* | (2013.01) | |
| *H04R 3/04* | (2006.01) | |
| *H04R 5/04* | (2006.01) | |
| *H04S 7/00* | (2006.01) | |
| *H04R 29/00* | (2006.01) | |
| *G16H 15/00* | (2018.01) | |
| *G06N 20/00* | (2019.01) | |
| *G10L 21/028* | (2013.01) | |
| *G10L 15/26* | (2006.01) | |
| *G16H 10/60* | (2018.01) | |
| *G16H 40/20* | (2018.01) | |
| *G10L 21/0216* | (2013.01) | |
| *G10L 21/0272* | (2013.01) | |

(52) U.S. Cl.
CPC .............. *G10L 15/20* (2013.01); *G10L 15/32* (2013.01); *G10L 17/06* (2013.01); *G10L 21/028* (2013.01); *G10L 25/78* (2013.01); *G10L 25/84* (2013.01); *G16H 15/00* (2018.01); *H04R 1/406* (2013.01); *H04R 3/005* (2013.01); *H04R 3/04* (2013.01); *H04R 5/04* (2013.01); *H04R 29/005* (2013.01); *H04S 7/307* (2013.01); *G10L 15/26* (2013.01); *G10L 21/0216* (2013.01); *G10L 21/0272* (2013.01); *G10L 2021/02166* (2013.01); *G16H 10/60* (2018.01); *G16H 40/20* (2018.01)

(58) Field of Classification Search
CPC ...... H04B 7/086; H04B 7/0417; H04R 1/406; H04R 3/005; H04R 3/02; H04S 7/30; B81B 7/00; G06K 9/00718; B60R 16/0373; G06T 7/20; G06V 40/23; G10K 11/17881; G10K 11/1783
USPC ............ 367/135; 370/286; 381/23.1, 92, 66, 381/71.4, 94.7; 700/94; 704/246, 248; 713/400; 379/406.03
See application file for complete search history.

(56) References Cited

U.S. PATENT DOCUMENTS

| | | | |
|---|---|---|---|
| 6,130,949 A | 10/2000 | Aoki | |
| 6,600,824 B1 | 7/2003 | Matsuo | |
| 6,748,086 B1* | 6/2004 | Venkatesh | H04M 9/082 381/71.4 |
| 8,666,090 B1 | 3/2014 | Townsend | |
| 8,885,815 B1* | 11/2014 | Velusamy | H04M 9/08 379/406.03 |
| 9,202,456 B2 | 12/2015 | Lee et al. | |
| 9,412,354 B1* | 8/2016 | Ramprashad | H04R 3/005 |
| 9,472,188 B1 | 10/2016 | Ouimette | |
| 9,508,357 B1 | 11/2016 | Krishnaswamy | |
| 9,516,409 B1* | 12/2016 | Ramprashad | H04R 1/406 |
| 9,532,138 B1* | 12/2016 | Allen | H04R 3/005 |
| 9,749,747 B1* | 8/2017 | Kriegel | H04R 5/02 |
| 9,858,340 B1 | 1/2018 | Frey et al. | |
| 9,866,308 B1 | 1/2018 | Bultan | |
| 9,892,744 B1 | 2/2018 | Salondis | |
| 9,900,685 B2 | 2/2018 | Varekar et al. | |
| 9,972,399 B2 | 5/2018 | Sundaram | |
| 10,037,756 B2 | 7/2018 | Pellom | |
| 10,090,000 B1* | 10/2018 | Tzirkel-Hancock | G10L 21/0232 |
| 10,313,786 B1* | 6/2019 | Bao | G10L 21/0232 |
| 10,381,022 B1 | 8/2019 | Chaudhuri | |
| 10,424,315 B1* | 9/2019 | Ganeshkumar | H03G 5/165 |
| 10,540,883 B1 | 1/2020 | Keil | |
| 10,777,214 B1* | 9/2020 | Shi | H04R 29/001 |
| 11,039,013 B1 | 6/2021 | Garrod | |
| 11,158,335 B1* | 10/2021 | Ganguly | H04R 1/406 |
| 2002/0048376 A1 | 4/2002 | Ukita | |
| 2002/0097885 A1 | 7/2002 | Birchfield | |
| 2003/0027600 A1 | 2/2003 | Kransy | |
| 2003/0033148 A1 | 2/2003 | Silverman et al. | |
| 2003/0051532 A1 | 3/2003 | Beaucoup | |
| 2003/0228023 A1 | 12/2003 | Burnett et al. | |
| 2003/0236663 A1 | 12/2003 | Dimitrova | |
| 2004/0240680 A1 | 12/2004 | Rui et al. | |
| 2005/0265562 A1 | 12/2005 | Rui | |
| 2006/0239471 A1 | 10/2006 | Mao | |
| 2006/0250998 A1* | 11/2006 | Beaucoup | H04R 3/005 370/286 |
| 2006/0262943 A1* | 11/2006 | Oxford | H04R 3/005 381/92 |
| 2007/0041586 A1 | 2/2007 | Stone et al. | |
| 2007/0053524 A1 | 3/2007 | Haulick et al. | |
| 2008/0091421 A1 | 4/2008 | Gustavson | |
| 2008/0167869 A1 | 7/2008 | Nakadai | |
| 2008/0170715 A1 | 7/2008 | Zhang | |
| 2008/0177536 A1 | 7/2008 | Sherwani | |
| 2009/0055178 A1* | 2/2009 | Coon | G10L 17/00 704/246 |
| 2009/0089053 A1 | 4/2009 | Wang | |
| 2009/0198495 A1* | 8/2009 | Hata | H04M 3/565 704/246 |
| 2009/0259466 A1 | 10/2009 | Stubley et al. | |
| 2010/0142327 A1 | 6/2010 | Kepesi | |
| 2010/0211387 A1 | 8/2010 | Chen | |
| 2010/0241426 A1 | 9/2010 | Zhang | |
| 2010/0296668 A1* | 11/2010 | Lee | G10K 11/17854 381/94.7 |
| 2011/0164761 A1 | 7/2011 | McCowan | |
| 2011/0288860 A1 | 11/2011 | Schevciw | |
| 2012/0123773 A1 | 5/2012 | Zeng | |
| 2012/0128175 A1* | 5/2012 | Visser | H04R 3/005 381/92 |
| 2012/0163610 A1 | 6/2012 | Sakagami | |
| 2012/0214544 A1 | 8/2012 | Shivappa et al. | |
| 2013/0035777 A1* | 2/2013 | Niemisto | G10L 21/0208 700/94 |
| 2013/0322643 A1 | 5/2013 | Every et al. | |
| 2013/0170666 A1 | 7/2013 | Ng et al. | |
| 2013/0204618 A1 | 8/2013 | Henry et al. | |
| 2013/0258813 A1* | 10/2013 | Herre | H04R 1/40 367/135 |
| 2013/0282373 A1 | 10/2013 | Visser et al. | |
| 2013/0304476 A1 | 11/2013 | Kim et al. | |
| 2013/0332156 A1 | 12/2013 | Tackin et al. | |
| 2014/0105416 A1* | 4/2014 | Huttunen | H04R 3/005 381/92 |
| 2014/0143582 A1* | 5/2014 | Kindred | H04R 25/554 713/400 |
| 2014/0149117 A1* | 5/2014 | Bakish | G10L 15/187 704/248 |
| 2014/0270231 A1 | 9/2014 | Dusan et al. | |
| 2014/0286497 A1* | 9/2014 | Thyssen | H04R 3/005 381/66 |
| 2014/0321664 A1 | 10/2014 | Huang et al. | |
| 2014/0334645 A1 | 11/2014 | Yun et al. | |
| 2014/0348342 A1 | 11/2014 | Tomlin et al. | |
| 2015/0063579 A1* | 3/2015 | Bao | H04M 9/082 381/66 |
| 2015/0302869 A1 | 10/2015 | Tomlin et al. | |
| 2015/0341722 A1* | 11/2015 | Iyengar | H04S 7/305 381/66 |
| 2016/0014490 A1 | 1/2016 | Bar Bracha et al. | |
| 2016/0035370 A1 | 2/2016 | Krini et al. | |
| 2016/0044411 A1* | 2/2016 | Tawada | H04R 3/005 381/92 |

(56) References Cited

U.S. PATENT DOCUMENTS

| | | | |
|---|---|---|---|
| 2016/0050488 A1 | 2/2016 | Matheja et al. | |
| 2016/0073203 A1* | 3/2016 | Kuriger | H04R 25/43 |
| | | | 381/23.1 |
| 2016/0322055 A1 | 3/2016 | Sainath et al. | |
| 2016/0189728 A1* | 6/2016 | Chen | G10L 21/0208 |
| | | | 704/246 |
| 2016/0261951 A1 | 9/2016 | Matheja et al. | |
| 2017/0047079 A1 | 2/2017 | Hiroe | |
| 2017/0257709 A1 | 9/2017 | Cohen et al. | |
| 2017/0287470 A1 | 10/2017 | Pellom et al. | |
| 2017/0307721 A1 | 10/2017 | Sugiyama et al. | |
| 2018/0176679 A1 | 6/2018 | Lu et al. | |
| 2018/0197559 A1* | 7/2018 | Orescanin | H04R 3/005 |
| 2018/0270565 A1* | 9/2018 | Ganeshkumar | H04R 3/005 |
| 2018/0294000 A1 | 10/2018 | Steele | |
| 2018/0308496 A1 | 10/2018 | Lee | |
| 2018/0309496 A1* | 10/2018 | Lee | H04L 5/0044 |
| 2018/0374495 A1 | 12/2018 | Fienberg et al. | |
| 2019/0046126 A1 | 2/2019 | Owen et al. | |
| 2019/0051375 A1 | 2/2019 | Owen et al. | |
| 2019/0058847 A1 | 2/2019 | Mayer et al. | |
| 2019/0189144 A1* | 6/2019 | Dusan | H04R 1/406 |
| 2019/0208318 A1* | 7/2019 | Chowdhary | B81B 7/00 |
| 2019/0272905 A1* | 9/2019 | Almendro Barreda | G10L 15/26 |
| 2019/0318743 A1 | 10/2019 | Reshef et al. | |
| 2019/0341050 A1 | 11/2019 | Diamant et al. | |
| 2019/0373362 A1 | 12/2019 | Ansai et al. | |
| 2019/0385635 A1* | 12/2019 | Shahen Tov | G10L 25/21 |
| 2020/0034113 A1* | 1/2020 | Holst, III | G06F 3/03544 |
| 2020/0066295 A1 | 2/2020 | Karimian-Azar et al. | |
| 2020/0098346 A1* | 3/2020 | Kemmerer | G10K 11/16 |
| 2020/0184985 A1* | 6/2020 | Nesta | H04S 3/008 |
| 2020/0213726 A1 | 7/2020 | Dyrolm | |
| 2020/0312315 A1 | 10/2020 | Li et al. | |
| 2020/0335088 A1 | 10/2020 | Gao et al. | |
| 2020/0349928 A1 | 11/2020 | Mandal et al. | |
| 2020/0349950 A1 | 11/2020 | Yoshioka et al. | |
| 2020/0374624 A1* | 11/2020 | Koschak | H04R 3/12 |
| 2020/0395003 A1 | 12/2020 | Sharma et al. | |
| 2020/0395109 A1* | 12/2020 | Owen | G16H 15/00 |
| 2020/0410045 A1 | 12/2020 | Vozilla et al. | |
| 2021/0021927 A1 | 1/2021 | Harke et al. | |
| 2021/0035563 A1 | 2/2021 | Cartwright et al. | |
| 2021/0065686 A1* | 3/2021 | Rao | G10L 15/22 |
| 2021/0098098 A1* | 4/2021 | Pinto | G16H 10/60 |
| 2021/0116519 A1 | 4/2021 | Weiss | |
| 2021/0134280 A1* | 5/2021 | Kurtz | G10L 25/84 |
| 2021/0193131 A1 | 6/2021 | Hook | |
| 2021/0210200 A1* | 7/2021 | Gallopyn | G06F 40/30 |
| 2021/0217432 A1* | 7/2021 | Zheng | G10L 25/57 |
| 2021/0233652 A1* | 7/2021 | Owen | G16H 40/20 |
| 2021/0241782 A1* | 8/2021 | Ganeshkumar | G10L 21/0232 |
| 2021/0243412 A1* | 8/2021 | Owen | H04R 3/005 |
| 2021/0350814 A1* | 11/2021 | Sharma | G10L 15/32 |
| 2021/0350815 A1* | 11/2021 | Sharma | G16H 15/00 |
| 2021/0352406 A1* | 11/2021 | Sharma | H04R 5/04 |

OTHER PUBLICATIONS

Cornelis, B., Moonen, M. and Wouters, J., "Binaural voice activity detection for MWF-based noise reduction in binaural hearing aids,", 2011, 2011 19th European Signal Processing Conference, pp. 486-490 (Year: 2011).

Non-Final Office Action issued in related U.S. Appl. No. 17/315,916 dated Jul. 14, 2021.

Non-Final Office Action issued in related U.S. Appl. No. 17/315,892 dated Jul. 14, 2021.

Non-Final Office Action issued in related U.S. Appl. No. 17/315,829 dated Jul. 16, 2021.

Non-Final Office Action issued in related U.S. Appl. No. 17/315,955 dated Jul. 28, 2021.

Yoshioka et al. "Meeting Transcription Using Asynchronous Distant Microphones," INTERSPEECH 2019. Retrieved on Jul. 7, 2021.

Dvorkind et al., "Time difference of Arrival Estimation of Speech Source in a Noisy and Reverberant Environment," CCIT Report #457, Dec. 2003, Retrieved on Apr. 4, 2021.

Internanional Search Report and Written Opinion issued in PCT/US2021/031516 dated Aug. 9, 2021.

International Search Report and Written Opinion issued in PCT/US2021/031508 dated Aug. 6, 2021.

International Search Report and Written Opinion issued in PCT/US2021/031363 dated Aug. 26, 2021.

International Search Report and Written Opinion issued in PCT/US2021/031369 dated Aug. 26, 2021.

International Search Report and Written Opinion issued in PCT/US2021/031374 dated Aug. 16, 2021.

International Search Report and Written Opinion issued in PCT/US2021/031378 dated Sep. 8, 2021.

International Search Report and Written Opinion issued in PCT/US2021/031498 dated Aug. 10, 2021.

International Search Report and Written Opinion issued in PCT/US2021/031504 dated Aug. 6, 2021.

International Search Report and Written Opinion issued in PCT/US2021/031512 dated Aug. 16, 2021.

Thomas et al., "Analyzing Convolutional Neural Networks for Speech Activity Detection in Mismatched Acoustic Conditions," IEEE International Conference on Acoustic, Speech and Signal Processing (2014).

* cited by examiner

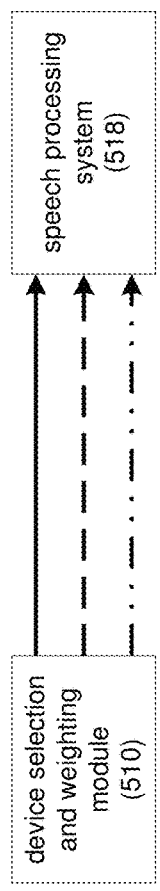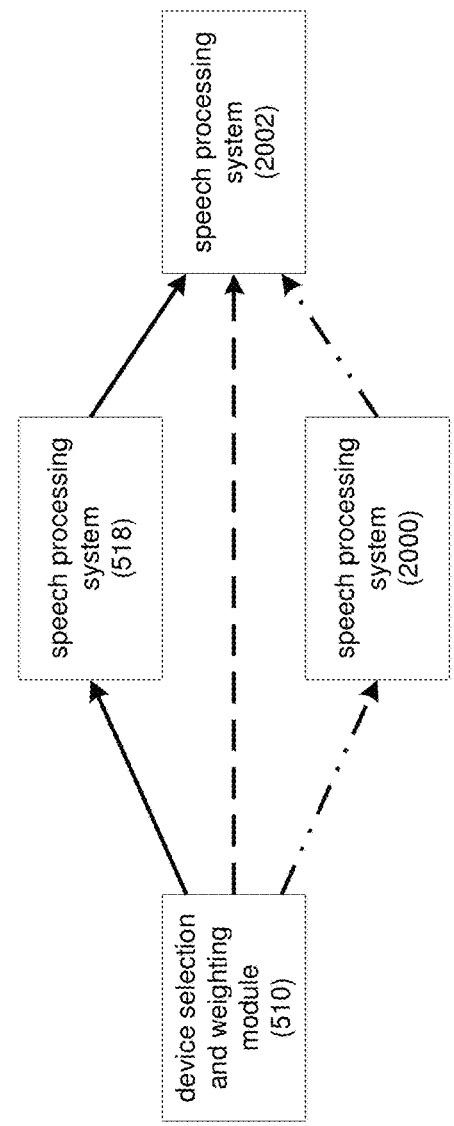

SYSTEM AND METHOD FOR MULTI-MICROPHONE AUTOMATED CLINICAL DOCUMENTATION

RELATED APPLICATION(S)

This application claims the benefit of the following U.S. Provisional Application No. 63/022,269 filed on 8 May 2020, the contents of which are all incorporated herein by reference.

BACKGROUND

Automated Clinical Documentation (ACD) may be used, e.g., to turn transcribed conversational (e.g., physician, patient, and/or other participants such as patient's family members, nurses, physician assistants, etc.) speech into formatted (e.g., medical) reports. Such reports may be reviewed, e.g., to assure accuracy of the reports by the physician, scribe, etc.

The process of capturing speech may include distant conversation automated speech recognition (DCASR). DCASR includes multiple microphone systems configured to record and recognize speech of one or more speakers (e.g., a microphone array and a single mobile microphone carried by a speaker). Conventional approaches to DCASR are subject to various challenges. For example, signal acquisition via a number of microphone systems (e.g., one or more microphone arrays and one or more mobile microphones) may be problematic. For example, when beamforming with single microphones, there are single channel noise reduction and de-reverberation methods that cannot be applied to multiple microphone systems. Additionally, conventional approaches to DCASR are unable to manage the combination of enhanced signals from various devices in a room. Conventional approaches to DCASR may encounter issues when locating where the speakers are at any given time, tracking their movements, and then identifying their identify. This may result in less accurate text transcriptions of recorded speech. In addition, an automated speech recognition (ASR) system, that converts the audio to text, may be unable to process the various metadata and audio signals from multiple sources (e.g., multiple microphone systems).

SUMMARY OF DISCLOSURE

In one implementation, a computer-implemented method executed by a computer may include but is not limited to receiving a plurality of predefined beams associated with a microphone array. A plurality of predefined nulls associated with the microphone array may be received. One or more predefined beams from the plurality of predefined beams or one or more predefined nulls from the plurality of predefined nulls may be selected. A microphone array may obtain audio encounter information, via the microphone array, using at least one of the one or more selected beams and the one or more selected nulls.

One or more of the following features may be included. The plurality of predefined beams may include one or more predefined beams configured to receive audio encounter information from one or more target speaker locations within an acoustic environment. The plurality of predefined nulls may include one or more predefined nulls configured to limit receiving audio encounter information from the one or more target speaker locations within the acoustic environment. Speaker metadata associated with one or more portions of audio encounter information may be received. Selecting at least one of the one or more beams and the one or more nulls may include selecting at least one of the one or more beams and the one or more nulls based upon, at least in part, the speaker metadata associated with the one or more portions of the audio encounter information. Selecting at least one of the one or more beams and the one or more nulls based upon, at least in part, the speaker metadata associated with the one or more portions of the audio encounter information may include selecting the one or more predefined beams configured to receive audio encounter information from the one or more target speaker locations within the acoustic environment based upon, at least in part, the speaker metadata associated with the one or more portions of the audio encounter information. Selecting at least one of the one or more beams and the one or more nulls based upon, at least in part, the speaker metadata associated with the one or more portions of the audio encounter information may include selecting the one or more predefined nulls configured to limit receiving audio encounter information from the one or more target speaker locations within the acoustic environment based upon, at least in part, the speaker metadata associated with the one or more portions of the audio encounter information.

In another implementation, a computer program product resides on a computer readable medium and has a plurality of instructions stored on it. When executed by a processor, the instructions cause the processor to perform operations including but not limited to receiving a plurality of predefined beams associated with a microphone array. A plurality of predefined nulls associated with the microphone array may be received. One or more predefined beams from the plurality of predefined beams or one or more predefined nulls from the plurality of predefined nulls may be selected. A microphone array may obtain audio encounter information, via the microphone array, using at least one of the one or more selected beams and the one or more selected nulls.

One or more of the following features may be included. The plurality of predefined beams may include one or more predefined beams configured to receive audio encounter information from one or more target speaker locations within an acoustic environment. The plurality of predefined nulls may include one or more predefined nulls configured to limit receiving audio encounter information from the one or more target speaker locations within the acoustic environment. Speaker metadata associated with one or more portions of audio encounter information may be received. Selecting at least one of the one or more beams and the one or more nulls may include selecting at least one of the one or more beams and the one or more nulls based upon, at least in part, the speaker metadata associated with the one or more portions of the audio encounter information. Selecting at least one of the one or more beams and the one or more nulls based upon, at least in part, the speaker metadata associated with the one or more portions of the audio encounter information may include selecting the one or more predefined beams configured to receive audio encounter information from the one or more target speaker locations within the acoustic environment based upon, at least in part, the speaker metadata associated with the one or more portions of the audio encounter information. Selecting at least one of the one or more beams and the one or more nulls based upon, at least in part, the speaker metadata associated with the one or more portions of the audio encounter information may include selecting the one or more predefined nulls configured to limit receiving audio encounter information from the one or more target speaker locations within the acoustic environment based upon, at least in part, the speaker metadata associated with the one or more portions of the audio encounter information.

In another implementation, a computing system includes a processor and memory is configured to perform operations including but not limited to, receiving a plurality of predefined beams associated with a microphone array. The processor may be further configured to receive a plurality of predefined nulls associated with the microphone array. The processor may be further configured to select at least one of: one or more predefined beams from the plurality of predefined beams, thus defining one or more selected beams and one or more predefined nulls from the plurality of predefined nulls, thus defining one or more selected nulls. The processor may be further configured to obtain audio encounter information, via the microphone array, using at least one of the one or more selected beams and the one or more selected nulls.

One or more of the following features may be included. The plurality of predefined beams may include one or more predefined beams configured to receive audio encounter information from one or more target speaker locations within an acoustic environment. The plurality of predefined nulls may include one or more predefined nulls configured to limit receiving audio encounter information from the one or more target speaker locations within the acoustic environment. Speaker metadata associated with one or more portions of audio encounter information may be received. Selecting at least one of the one or more beams and the one or more nulls may include selecting at least one of the one or more beams and the one or more nulls based upon, at least in part, the speaker metadata associated with the one or more portions of the audio encounter information. Selecting at least one of the one or more beams and the one or more nulls based upon, at least in part, the speaker metadata associated with the one or more portions of the audio encounter information may include selecting the one or more predefined beams configured to receive audio encounter information from the one or more target speaker locations within the acoustic environment based upon, at least in part, the speaker metadata associated with the one or more portions of the audio encounter information. Selecting at least one of the one or more beams and the one or more nulls based upon, at least in part, the speaker metadata associated with the one or more portions of the audio encounter information may include selecting the one or more predefined nulls configured to limit receiving audio encounter information from the one or more target speaker locations within the acoustic environment based upon, at least in part, the speaker metadata associated with the one or more portions of the audio encounter information.

The details of one or more implementations are set forth in the accompanying drawings and the description below. Other features and advantages will become apparent from the description, the drawings, and the claims.

BRIEF DESCRIPTION OF THE DRAWINGS

FIGS. 20A-20B are diagrammatic views of the processing of audio encounter information received by various microphone systems using various speech processing system configurations according to various implementations of the automated clinical documentation process of FIG. 1.

Like reference symbols in the various drawings indicate like elements.

DETAILED DESCRIPTION OF THE PREFERRED EMBODIMENTS

Figure 1:
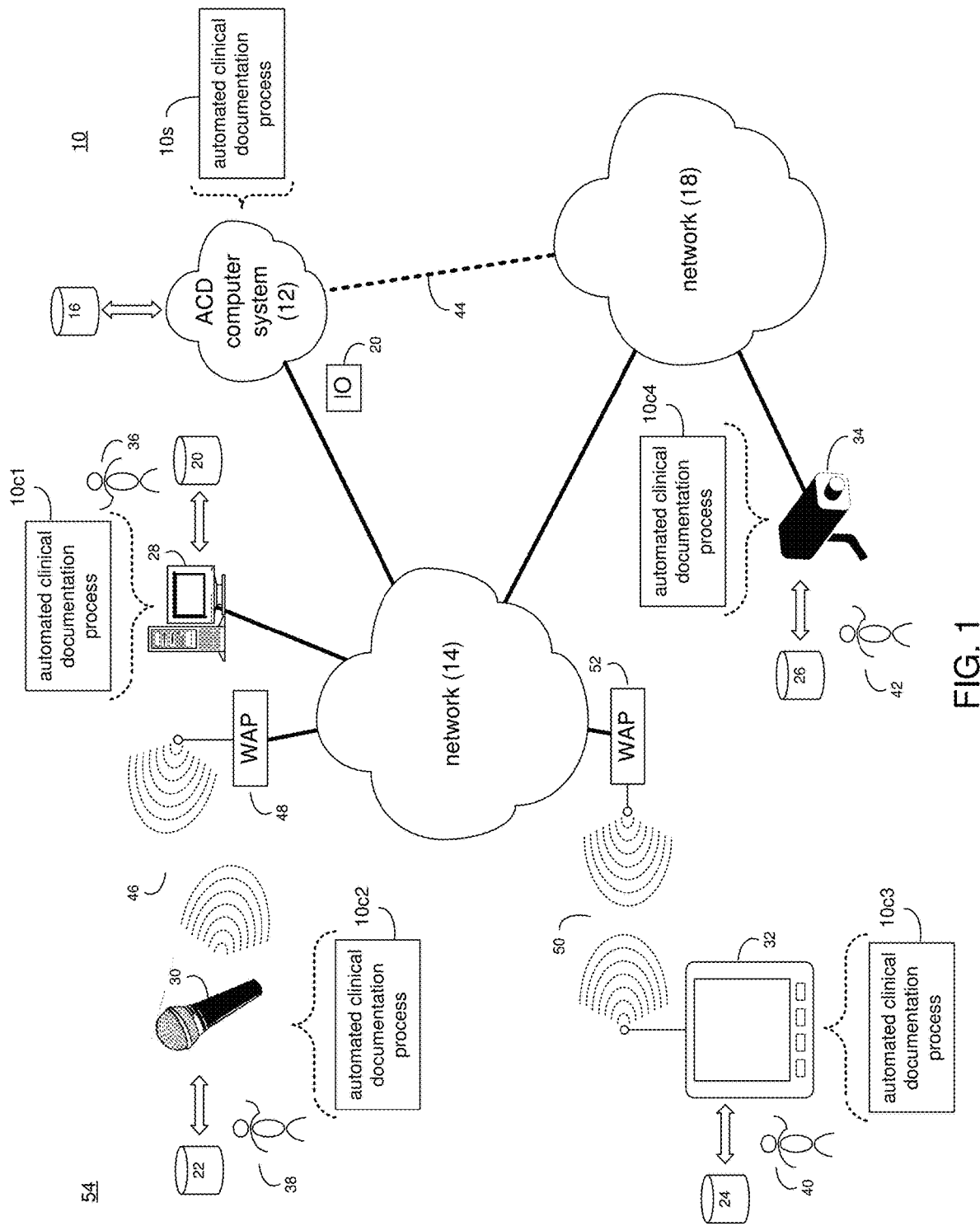
FIG. 1 is a diagrammatic view of an automated clinical documentation computer system and an automated clinical documentation process coupled to a distributed computing network.

System Overview:

Referring to FIG. 1, there is shown automated clinical documentation process 10. As will be discussed below in greater detail, automated clinical documentation process 10 may be configured to automate the collection and processing of clinical encounter information to generate/store/distribute medical records.

Automated clinical documentation process 10 may be implemented as a server-side process, a client-side process, or a hybrid server-side/client-side process. For example, automated clinical documentation process 10 may be implemented as a purely server-side process via automated clinical documentation process 10s. Alternatively, automated clinical documentation process 10 may be implemented as a purely client-side process via one or more of automated clinical documentation process 10c1, automated clinical documentation process 10c2, automated clinical documentation process 10c3, and automated clinical documentation process 10c4. Alternatively still, automated clinical documentation process 10 may be implemented as a hybrid server-side/client-side process via automated clinical documentation process 10s in combination with one or more of automated clinical documentation process 10c1, automated clinical documentation process 10c2, automated clinical documentation process 10c3, and automated clinical documentation process 10c4.

Accordingly, automated clinical documentation process 10 as used in this disclosure may include any combination of automated clinical documentation process 10s, automated clinical documentation process 10c1, automated clinical documentation process 10c2, automated clinical documentation process 10c3, and automated clinical documentation process 10c4.

Automated clinical documentation process 10s may be a server application and may reside on and may be executed by automated clinical documentation (ACD) computer system 12, which may be connected to network 14 (e.g., the Internet or a local area network). ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACD computer system 12 may execute one or more operating systems, examples of which may include but are not limited to: Microsoft Windows Server™; Redhat Linux™, Unix, or a custom operating system, for example.

The instruction sets and subroutines of automated clinical documentation process 10s, which may be stored on storage device 16 coupled to ACD computer system 12, may be executed by one or more processors (not shown) and one or more memory architectures (not shown) included within ACD computer system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from automated clinical documentation process 10s, automated clinical documentation process 10c1, automated clinical documentation process 10c2, automated clinical documentation process 10c3 and/or automated clinical documentation process 10c4 to ACD computer system 12. Examples of IO request 20 may include but are not limited to data write requests (i.e. a request that content be written to ACD computer system 12) and data read requests (i.e. a request that content be read from ACD computer system 12).

The instruction sets and subroutines of automated clinical documentation process 10c1, automated clinical documentation process 10c2, automated clinical documentation process 10c3 and/or automated clinical documentation process 10c4, which may be stored on storage devices 20, 22, 24, 26 (respectively) coupled to ACD client electronic devices 28, 30, 32, 34 (respectively), may be executed by one or more processors (not shown) and one or more memory architectures (not shown) incorporated into ACD client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACD client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACD computer system 12 directly through network 14 or through secondary network 18. Further, ACD computer system 12 may be connected to network 14 through secondary network 18, as illustrated with link line 44.

The various ACD client electronic devices (e.g., ACD client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACD client electronic devices (e.g., ACD client electronic devices 28, 30, 32, 34) may each execute an operating system, examples of which may include but are not limited to Microsoft Windows™, Apple Macintosh™, Redhat Linux™, or a custom operating system, wherein the combination of the various ACD client electronic devices (e.g., ACD client electronic devices 28, 30, 32, 34) and ACD computer system 12 may form modular ACD system 54.

Figure 2:
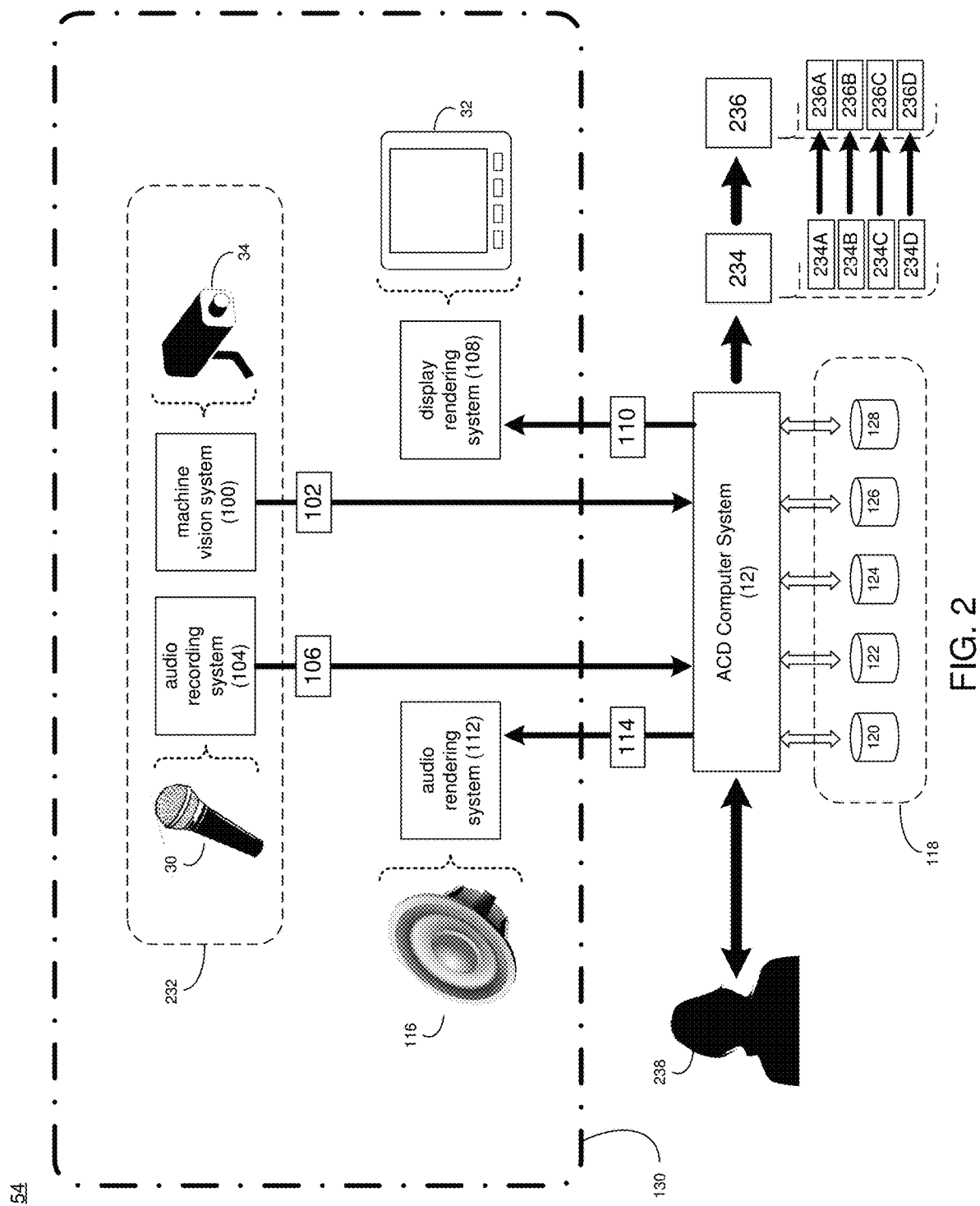
FIG. 2 is a diagrammatic view of a modular ACD system incorporating the automated clinical documentation computer system of FIG. 1.

Referring also to FIG. 2, there is shown a simplified example embodiment of modular ACD system 54 that is configured to automate clinical documentation. Modular ACD system 54 may include: machine vision system 100 configured to obtain machine vision encounter information 102 concerning a patient encounter; audio recording system 104 configured to obtain audio encounter information 106 concerning the patient encounter; and a computer system (e.g., ACD computer system 12) configured to receive machine vision encounter information 102 and audio encounter information 106 from machine vision system 100 and audio recording system 104 (respectively). Modular ACD system 54 may also include: display rendering system 108 configured to render visual information 110; and audio rendering system 112 configured to render audio information 114, wherein ACD computer system 12 may be configured to provide visual information 110 and audio information 114 to display rendering system 108 and audio rendering system 112 (respectively).

Example of machine vision system 100 may include but are not limited to: one or more ACD client electronic devices (e.g., ACD client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACD client electronic devices (e.g., ACD client electronic device 32, examples of which may include but are not limited to a tablet computer, a computer monitor, and a smart television). Examples of audio rendering system 112 may include but are not limited to: one or more ACD client electronic devices (e.g., audio rendering device 116, examples of which may include but are not limited to a speaker system, a headphone system, and an earbud system).

As will be discussed below in greater detail, ACD computer system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACD system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACD client electronic devices (e.g., ACD client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACD client electronic devices (e.g., ACD client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACD client electronic devices (e.g., ACD client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACD client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACD computer system 12 may include a plurality of discrete computer systems. As discussed above, ACD computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACD computer system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
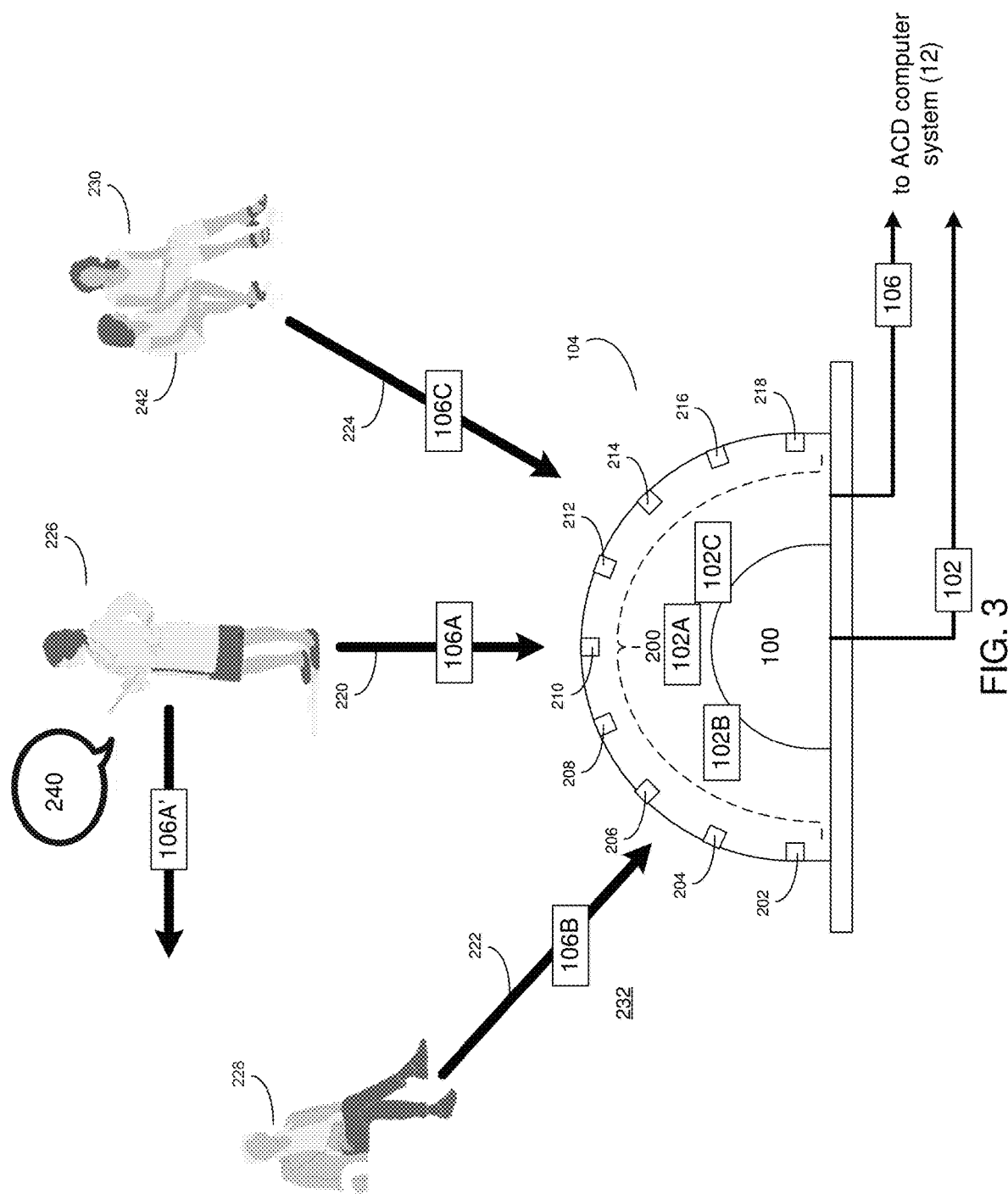
FIG. 3 is a diagrammatic view of a mixed-media ACD device included within the modular ACD system of FIG. 2.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACD system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACD system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACD system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACD system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACD system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACD system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACD device 232. For example, mixed-media ACD device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACD system 54 may be configured to include a plurality of mixed-media ACD devices (e.g., mixed-media ACD device 232) when the above-described clinical environment is larger or a higher level of resolution is desired.

Modular ACD system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACD device 232 (and machine vision system 100/audio recording system 104 included therein) may be configured to monitor one or more encounter participants (e.g., encounter participants 226, 228, 230) of a patient encounter.

Specifically, machine vision system 100 (either as a stand-alone system or as a component of mixed-media ACD device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACD system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACD computer system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACD system 54 (and/or mixed-media ACD device 232) is configured, ACD computer system 12 may be included within mixed-media ACD device 232 or external to mixed-media ACD device 232.

As discussed above, ACD computer system 12 may execute all or a portion of automated clinical documentation process 10, wherein the instruction sets and subroutines of automated clinical documentation process 10 (which may be stored on one or more of e.g., storage devices 16, 20, 22, 24, 26) may be executed by ACD computer system 12 and/or one or more of ACD client electronic devices 28, 30, 32, 34.

The Automated Clinical Documentation Process:

In some implementations consistent with the present disclosure, systems and methods may be provided for speaker diarization and distant speech recognition using spatial and spectral information. For example, distant conversation automated speech recognition (DCASR) may include multiple microphone systems configured to record and recognize speech of one or more speakers (e.g., a microphone array and a single mobile microphone carried by a speaker). Conventional approaches to DCASR are subject to various challenges when utilizing signals from multiple microphones. For example, conventional beamforming techniques combine the multiple microphone signals via spatial filtering, but these are mostly limited to single microphone array devices (i.e. they typically do not provide a mechanism for combining various microphones not part of an array, nor different microphone arrays deployed in a room operating as independent devices). Conventional techniques also allow for single channel noise reduction and de-reverberation techniques. However, such techniques do not account for the spatial information that maybe available. Additionally, conventional approaches to DCASR are unable to manage the combination of enhanced signals from various devices in the room. In some implementations, conventional approaches to DCASR may encounter issues when locating where the speakers are at any given time, tracking their movements, and then identifying their identify. This may result in less accurately diarized text transcriptions (i.e., text transcriptions with speaker labels to define who said what and when in a conversation). In addition, an ASR system, that converts the audio to text, may be unable to process the various metadata and audio signals from multiple sources (e.g., multiple microphone systems).

Accordingly, implementations of the present disclosure may address these challenges experienced by conventional approaches to DCASR by predefining beamforming configurations based upon, at least in part, information associated with an acoustic environment; selecting particular beam patterns and/or null patterns for particular locations (e.g., where beams and nulls are selected to point to certain locations in a room, some which may have a high probability of being occupied by a particular speaker); voice activity detection and localization using spatial and spectral information; speaker identification with spatial and spectral information; and alignment of audio streams from multiple microphone systems based upon, at least in part, voice activity detection. For example, automated clinical documentation process 10 may include various hardware and/or software modules configured to perform various DCASR functions within the scope of the present disclosure.

Figure 4:
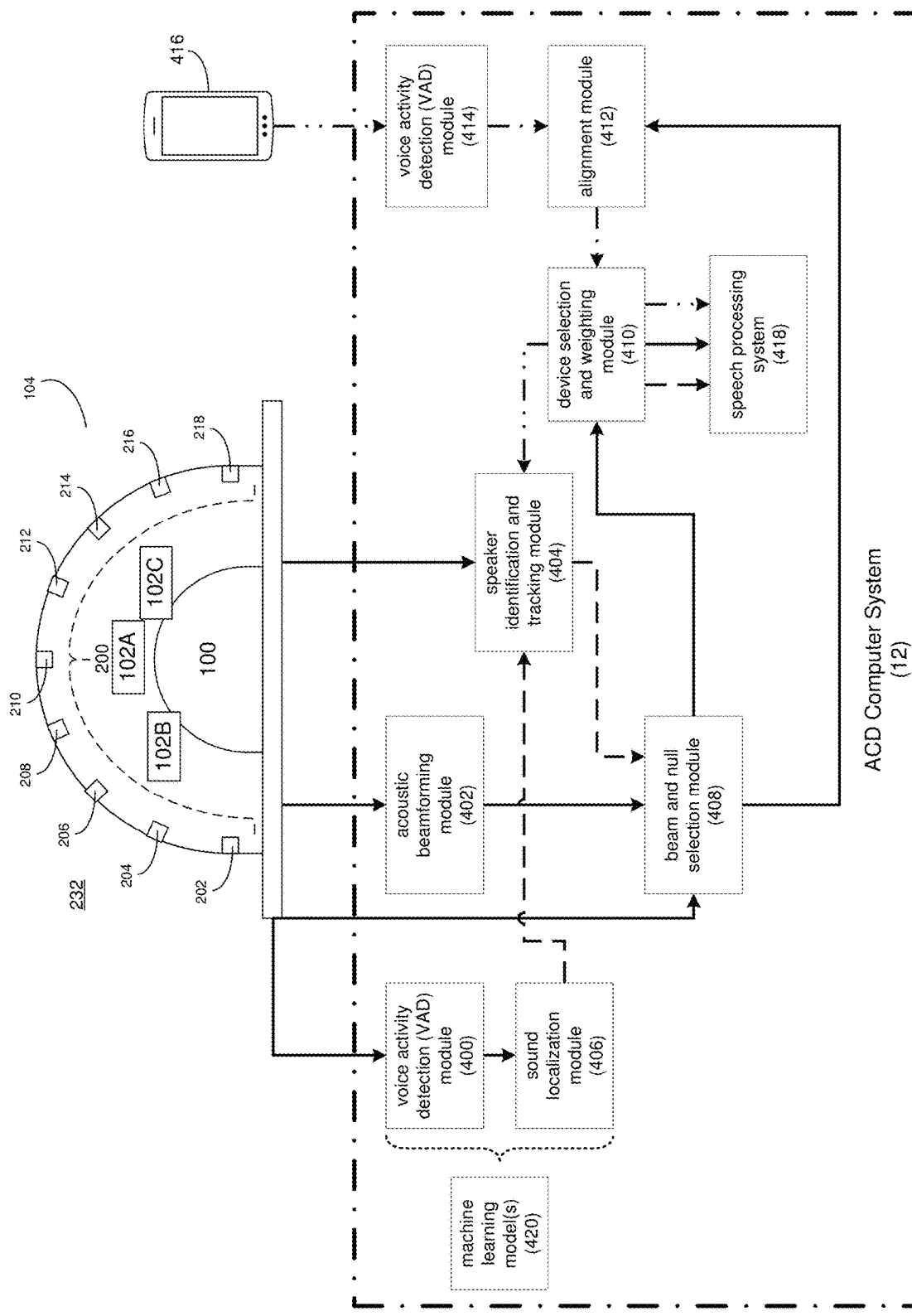
FIG. 4 is a diagrammatic view of various modules included within a ACD computer device within the modular ACD system of FIG. 2.

Referring also to FIG. 4 and in some implementations, machine vision system 100 and audio recording system 104 may be combined into one package to form mixed-media ACD device 232. In this example, ACD computer system 12 may be configured to receive machine vision encounter information 102 and audio encounter information 106 from machine vision system 100 and audio recording system 104 (respectively). Specifically, ACD computer system 12 may receive the audio encounter information at a voice activity detection (VAD) module (e.g., VAD module 400); at an acoustic beamforming module (e.g., acoustic beamforming module 402); and/or at a speaker identification and tracking module (e.g., speaker identification and tracking module 404). In some implementations, ACD computer system 12 may also receive machine vision encounter information 102 at speaker identification and tracking module 404. In some implementations, VAD module 400 may communicate with sound localization module 406 to output metadata for speaker identification and tracking module 404. In some implementations, acoustic beamforming module 402 may be configured to provide a plurality of beams and/or a plurality of nulls to a beam and null selection module (e.g., beam and null selection module 408). Speaker identification and tracking module 404 may be configured to provide speaker identification and tracking information to beam and null selection module 408.

In some implementations, beam and null selection module 408 may be configured to provide an aligned audio stream from audio recording system 104 to a device selection and weighting module (e.g., device selection and weighting module 410). In addition, beam and null selection module 408 may be configured to provide the aligned audio stream to an alignment module (e.g., alignment module 412). Alignment module 412 may be configured to receive audio encounter information from a VAD module associated with a second microphone system (e.g., VAD module 414 associated with mobile electronic device 416). In some implementations, alignment module 412 may be configured to provide an aligned audio stream from mobile electronic device 416 to device selection and weighting module 410. In some implementations, device selection and weighting module 410 may provide the aligned audio stream from audio recording system 104, the aligned audio stream from mobile electronic device 416, and metadata from the other modules to one or more speech processing systems (e.g., speech processing system 418). In some implementations, speech processing system 418 may be an automated speech recognition (ASR) system.

As will be discussed in greater detail below, the combination of the various modules of ACD computer system 12/automated clinical documentation process 10 may be configured to improve DCASR by providing aligned audio encounter information from multiple microphone systems. In this manner, automated clinical documentation process 10 may improve distant speech recognition using spatial and spectral information determined by the various modules of ACD computer system 12/automated clinical documentation process 10.

Figure 5:
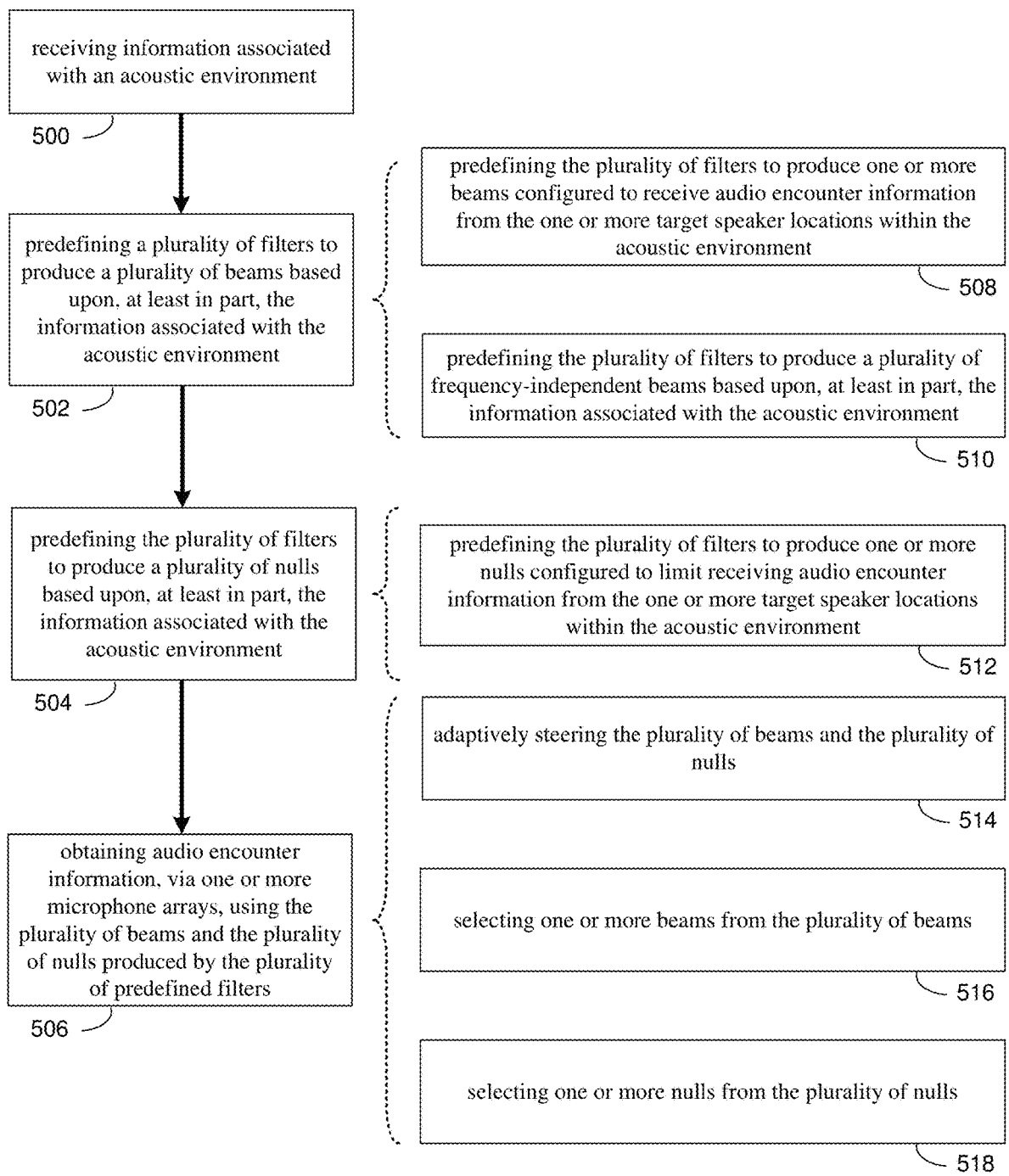
FIG. 5 is a flow chart of one implementation of the automated clinical documentation process of FIG. 1.
Figure 6:
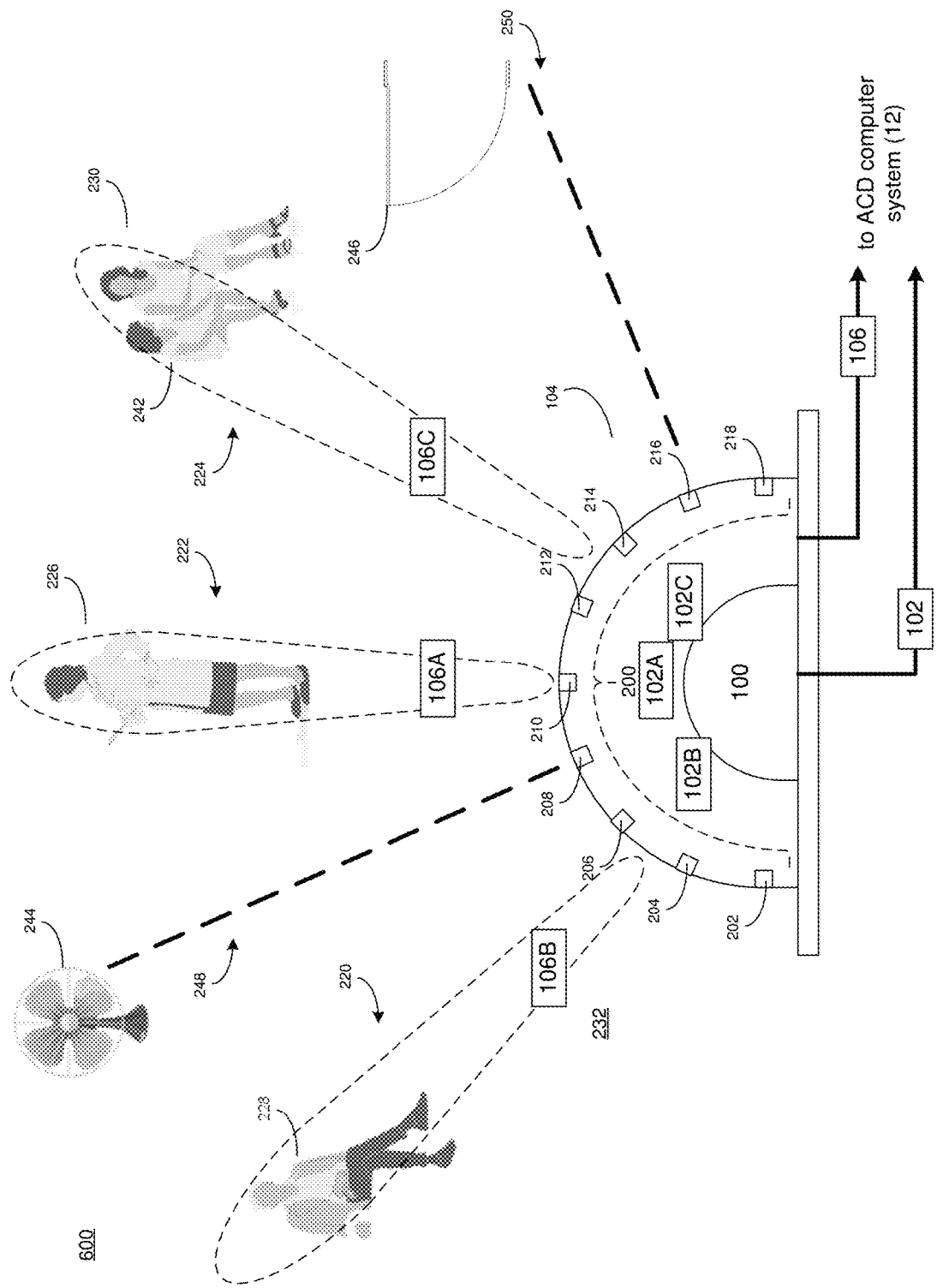
FIGS. 6-7 are diagrammatic views of a modular ACD system according to various implementations of the automated clinical documentation process of FIG. 1.
Figure 7:
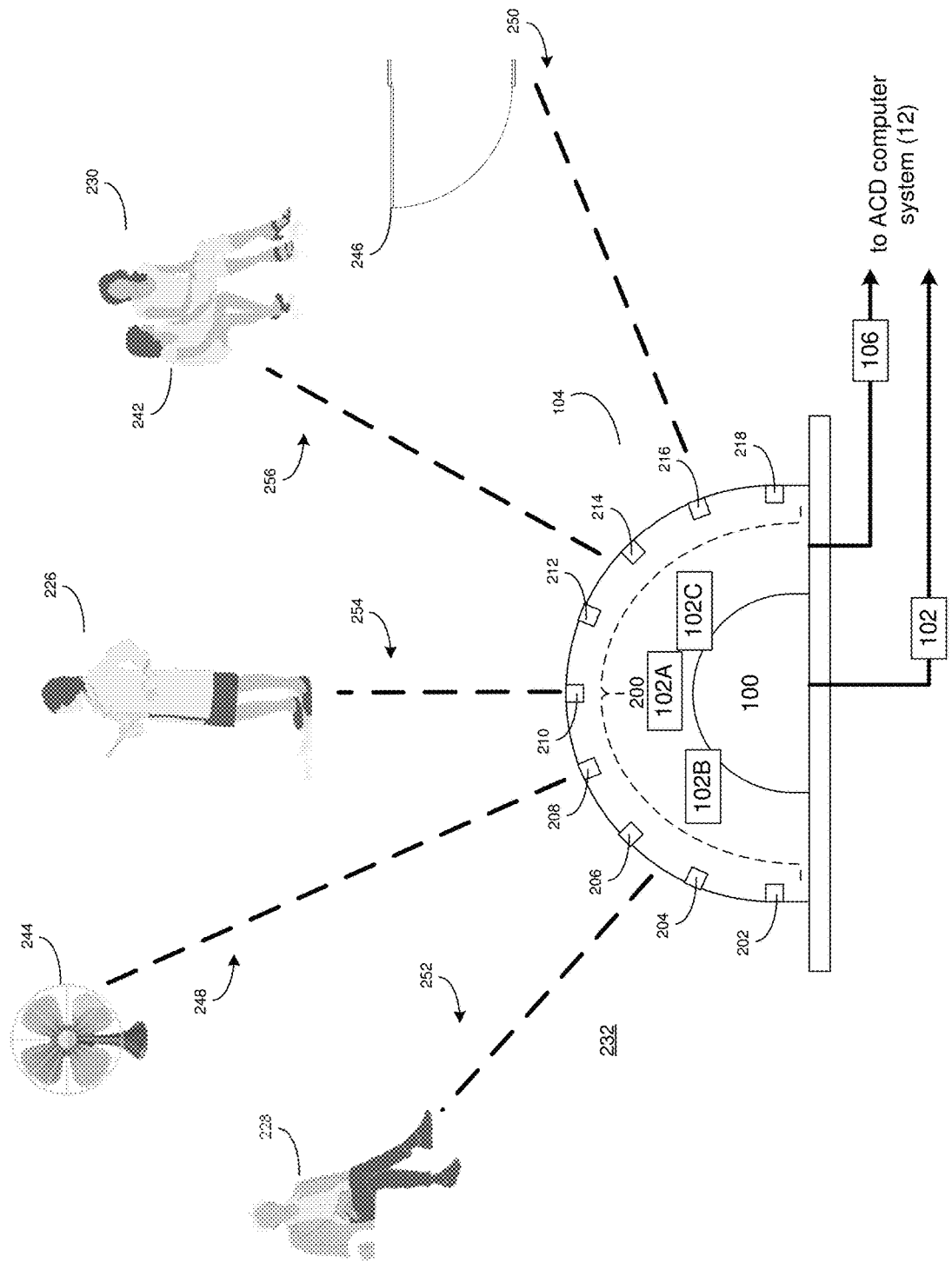

Referring also at least to FIGS. 5-7, automated clinical documentation process 10 may receive 500 information associated with an acoustic environment. A plurality of filters may be predefined 502 to produce a plurality of beams based upon, at least in part, the information associated with the acoustic environment. The plurality of filters may be predefined 504 to produce a plurality of nulls based upon, at least in part, the information associated with the acoustic environment. Audio encounter information may be obtained

506, via one or more microphone arrays, using the plurality of beams and the plurality of nulls produced by the plurality of predefined filters.

As will be discussed in greater detail below, automated clinical documentation process 10 may predefine or pre-compute a plurality of filters to produce beams and nulls for targeting specific speakers and/or noise sources to improve DCASR. As is known in the art, beamformers may use a set of filters associated with a set of input signals to generate a spatially filtered sensitivity pattern formed from beams and nulls with characteristics determined by the filters. As will be discussed in greater detail below, automated clinical documentation process 10 may receive 500 information associated with an acoustic environment and may predefine filters to produce beams and/or nulls to target or isolate specific speakers and/or noise sources. In this manner, automated clinical documentation process 10 may utilize acoustic environment information to predefine beams and nulls that may be selected for various situations (i.e., selecting certain beams and nulls when a patient is speaking to a medical professional and selecting other beams and nulls when the medical professional is speaking to the patient).

In some implementations, automated clinical documentation process 10 may receive 500 information associated with an acoustic environment. An acoustic environment may represent the layout and acoustic properties of a room or other space where multiple microphone systems may be deployed. For example, information associated with the acoustic environment may describe the type/dimensions of a room, the activity zones in the room where the participants are likely to be or operate, the acoustic properties of the room (e.g., the types of noise expected, range of reverberation, etc.), position of the microphone system(s) within the acoustic environment, etc. In some implementations, automated clinical documentation process 10 may provide a user interface to receive information associated with the acoustic environment. Accordingly, a user and/or automated clinical documentation process 10 may provide the information associated with an acoustic environment (e.g., via the user interface). However, it will be appreciated that the information associated with the acoustic environment may be received in various ways (e.g., default information for a default acoustic environment, automatically defined by automated clinical documentation process 10, etc.).

In some implementations, the information associated with the acoustic environment may indicate one or more target speaker locations within the acoustic environment. Referring also to FIG. 6 and in some implementations, suppose that acoustic environment 600 includes one or more encounter participants (e.g., encounter participants 226, 228, 230) of the above-described patient encounter. As described above, examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

In some implementations, automated clinical documentation process 10 may receive 500 information associated with acoustic environment 600 that indicates the location of encounter participants 226, 228, 230. In some implementations, the information associated with acoustic environment 600 may indicate locations within acoustic environment where the one or more target speakers are likely to be when speaking. For example, suppose automated clinical documentation process 10 determines that an examination table is positioned at approximately e.g., 45° from the base of microphone array 200. In this example, automated clinical documentation process 10 may determine that a patient is most likely to speak while sitting on or near the examination table at approximately 45° from the base of microphone array 200. Further suppose that automated clinical documentation process 10 determines that a doctor's desk is positioned at approximately e.g., 90° from the base of microphone array 200. In this example, automated clinical documentation process 10 may determine that a doctor is most likely to speak while sitting on or near the desk at approximately 90° from the base of microphone array 200. Additionally, suppose automated clinical documentation process 10 determines that a waiting area is positioned at approximately e.g., 120° from the base of microphone array 200. In this example, automated clinical documentation process 10 may determine that other patients or other third parties are most likely to speak from at approximately 120° from the base of microphone array 200. While three examples of relative locations for target speakers within an acoustic environment have been provided, it will be appreciated that the information associated with the acoustic environment may include any number of target speaker locations or probability-based target speaker locations for any number of target speakers within the scope of the present disclosure.

In some implementations, automated clinical documentation process 10 may predefine 502 a plurality of filters to produce a plurality of beams based upon, at least in part, the information associated with the acoustic environment. A beam may generally include a pattern of constructive interference among microphones of a microphone array that is generated by modifying the phase and/or amplitude of the signal at each microphone of the microphone array via a plurality of filters. The pattern of constructive interference may improve the signal processing performance of the microphone array. Predefining 502 a plurality of filters to produce a plurality of beams may generally include defining the plurality of beams at any point in time prior to obtaining 506 audio encounter information via the one or more microphone arrays. The plurality of filters may include a plurality of finite impulse response (FIR) filters configured to adjust the phase and/or amplitude of a signal at each microphone of a microphone array. Accordingly, automated clinical documentation process 10 may predefine the plurality of filters (e.g., the plurality of FIR filters) to produce a plurality of beams that are configured to "look" or orient in a particular direction based upon, at least in part, the information associated with the acoustic environment. In some implementations, automated clinical documentation process 10 may predefine 502 the plurality of filters to produce a plurality of beams by adjusting the phase and/or amplitude of the signal at each microphone of the microphone array.

For instance, automated clinical documentation process 10 may receive 500 information associated with acoustic environment and may determine how the acoustic properties of the acoustic environment impact beams deployed within the acoustic environment. For example, suppose that the information associated with the acoustic environment indicates that a particular reverberation level may be present at particular frequencies and at varying amplitudes at different parts of the acoustic environment. In this example, automated clinical documentation process 10 may predefine 502 the plurality of filters to produce a plurality of beams to account for the layout, acoustic properties, etc. of the acoustic environment. As will be discussed in greater detail below, by predefining 502 the plurality of filters to produce a plurality of beams, automated clinical documentation process 10 may allow for the selection of particular beams for various situations.

In some implementations, predefining 502 the plurality of filters to produce the plurality of beams based upon, at least in part, the information associated with the acoustic environment may include predefining 508 the plurality of filters to produce one or more beams configured to receive audio encounter information from the one or more target speaker locations within the acoustic environment. For example and referring again to FIG. 6, automated clinical documentation process 10 may predefine 508 the plurality of filters to produce one or more beams configured to receive audio encounter information from the one or more target speaker locations within the acoustic environment. Continuing with the above example, suppose that automated clinical documentation process 10 determines from the information associated with acoustic environment 600, that a patient is most likely to speak while sitting on or near the examination table at approximately 45° from the base of microphone array 200; a doctor is most likely to speak while sitting on or near the desk at approximately 90° from the base of microphone array 200; and that other patients or other third parties are most likely to speak from at approximately 120° from the base of microphone array 200. In this example, automated clinical documentation process 10 may predefine 508 the plurality of filters to produce beam 220 for receiving audio encounter information from a patient (e.g., encounter participant 228); beam 222 for receiving audio encounter information from a doctor (e.g., encounter participant 226); and beam 224 for receiving audio encounter information from another patient/third party (e.g., encounter participant 230). As will be discussed in greater detail below, automated clinical documentation process 10 may select particular beams for receiving audio encounter information when a specific participant is speaking.

In some implementations, predefining 502 the plurality of filters to produce a plurality of beams based upon, at least in part, the information associated with the acoustic environment may include predefining 510 the plurality of filters to produce a plurality of frequency-independent beams based upon, at least in part, the information associated with the acoustic environment. In some implementations, the spatial sensitivity to audio encounter information of a beam may be frequency-dependent. For example, for receiving high frequency signals, the beam of sensitivity may be narrow while the beam of sensitivity for low frequency signals may be wide. Accordingly, automated clinical documentation process 10 may predefine 510 the plurality of filters to produce a plurality of frequency-independent beams based upon, at least in part, the information associated with the acoustic environment. For example and as discussed above, automated clinical documentation process 10 may determine particular locations within an acoustic environment where speakers may be located when they speak based upon, at least in part, the information associated with the acoustic environment. Additionally, automated clinical documentation process 10 may receive acoustic properties of the acoustic environment. For example, automated clinical documentation process 10 may determine the location(s) and frequency characteristics of one or more noise sources within the acoustic environment. In this manner, automated clinical documentation process 10 may predefine 510 the plurality of filters to produce a plurality of frequency-independent beams that account for the acoustic properties of the acoustic environment while providing sufficient microphone sensitivity for frequency variations.

For example, automated clinical documentation process 10 may predefine 502 the plurality of filters to produce beams 220, 222, 224 by modifying the phase and/or amplitude of the signals of each microphone such that the beam is sufficiently sensitive to receive audio encounter information for target speakers within the acoustic environment regardless of the frequency. In this manner, automated clinical documentation process 10 may predefine 510 the plurality of filters to produce a plurality of frequency-independent beams (e.g., frequency-independent beams 220, 222, 224) based upon, at least in part, the information associated with the acoustic environment (e.g., acoustic environment 600).

In some implementations, automated clinical documentation process 10 may predefine 504 the plurality of filters to produce a plurality of nulls based upon, at least in part, the information associated with the acoustic environment. A null may generally include a pattern of destructive interference among microphones of a microphone array that is generated by modifying the phase and/or amplitude of the signal at each microphone of the microphone array. The pattern of destructive interference may limit the reception of signals by the microphone array. Predefining 504 the plurality of filters to produce a plurality of nulls may generally include defining the plurality of nulls at any point in time prior to obtaining 506 audio encounter information via one or more microphone arrays. As discussed above, the plurality of filters may include a plurality of finite impulse response (FIR) filters configured to adjust the phase and/or amplitude of a signal at each microphone of a microphone array. Accordingly, automated clinical documentation process 10 may predefine the plurality of filters (e.g., the plurality of FIR filters) to produce a plurality of nulls that are configured to "look" or orient in a particular direction based upon, at least in part, the information associated with the acoustic environment. In contrast to a beam, a null may limit or attenuate reception at the target direction. In some implementations, automated clinical documentation process 10 may predefine 504 the plurality of filters to produce a plurality of nulls by adjusting the phase and/or amplitude of the signal at each microphone of the microphone array.

For instance, automated clinical documentation process 10 may receive 500 information associated with acoustic environment and may determine how the acoustic properties of the acoustic environment impact beams deployed within the acoustic environment. For example and as discussed above, suppose that the information associated with the acoustic environment indicates that a particular noise signal (e.g., sound of an air-conditioning system) may be present at particular frequencies and at varying amplitudes at different parts of the acoustic environment. In this example, automated clinical documentation process 10 may predefine 504 the plurality of filters to produce a plurality of nulls to limit the reception of noise signals. As will be discussed in greater detail below, by predefining 504 the plurality of filters to produce the plurality of nulls, automated clinical documentation process 10 may allow for the selection of particular nulls for various situations.

In some implementations, automated clinical documentation process 10 may predefine 504 the plurality of filters to produce one or more nulls configured to limit receiving noise signals from one or more noise sources based upon, at least in part, the information associated with the acoustic environment. For example and referring again to FIG. 6, suppose that automated clinical documentation process 10 determines from the information associated with acoustic environment 600 that a noise source (e.g., fan 244) is positioned e.g., approximately 70° from the base of microphone array 200 and that a second noise source (e.g., a doorway to a busy hallway 246) is positioned e.g., approximately 150° from the base of microphone array 200. In this example, automated clinical documentation process 10 may predefine 512 the plurality of filters to produce null 248 to limit receiving noise signals from a first noise source (e.g., fan 244) and null 250 to limit receiving noise signals from a second noise source (e.g., a doorway to a busy hallway 246). While an example of predefining 504 the plurality of filters to produce two nulls for two noise sources has been described, it will be appreciated that automated clinical documentation process 10 may predefine 504 the plurality of filters to produce any number of nulls for any number of noise sources within the scope of the present disclosure. In some implementations, automated clinical documentation process 10 may select particular nulls to limit receiving noise signals for various situations.

In some implementations, predefining 504 the plurality of filters to produce the plurality of nulls based upon, at least in part, the information associated with the acoustic environment may include predefining 512 the plurality of filters to produce one or more nulls to limit receiving audio encounter information from the one or more target speaker locations within the acoustic environment. For example and referring again to FIG. 6, automated clinical documentation process 10 may predefine 512 the plurality of filters to produce one or more nulls to limit receiving audio encounter information from the one or more target speaker locations within the acoustic environment. Continuing with the above example, suppose that automated clinical documentation process 10 determines from the information associated with acoustic environment 600, that a patient is most likely to speak while sitting on or near the examination table at approximately 45° from the base of microphone array 200; a doctor is most likely to speak while sitting on or near the desk at approximately 90° from the base of microphone array 200; and that other patients or other third parties are most likely to speak from at approximately 120° from the base of microphone array 200.

In this example and referring also to FIG. 7, automated clinical documentation process 10 may predefine 504 the plurality of filters to produce null 252 to limit receiving audio encounter information from a patient (e.g., encounter participant 228); null 254 to limit receiving audio encounter information from a doctor (e.g., encounter participant 226); and null 256 to limit receiving audio encounter information from another patient/third party (e.g., encounter participant 230). As will be discussed in greater detail below, automated clinical documentation process 10 may select particular nulls to limit audio encounter information from other speakers to focus on audio encounter information from a particular target speaker.

However, in another example, suppose a patient (e.g., encounter participant 228) and a doctor (e.g., encounter participant 226) are talking over each other for a short duration (i.e., "overalled speech"). Automated clinical documentation process 10 may form two output signals where a first signal is the sum a beam pattern oriented toward the doctor (e.g., encounter participant 226) and a null oriented toward the patient (e.g., encounter participant 228); and a second signal is the sum a beam pattern oriented toward the patient (e.g., encounter participant 228) and a null oriented toward the doctor (e.g., encounter participant 226). In this manner, the combination of the two signals formed from the beams and nulls defined for each signal may have a better chance of accurately transcribing what the doctor and the patient said.

In some implementations, automated clinical documentation process 10 may obtain 506 audio encounter information, via one or more microphone arrays, using the plurality of beams and the plurality of nulls produced by the plurality of predefined filters. As discussed above, in the example of audio signals, one or more microphone arrays may utilize beams and nulls to audio encounter information from particular speakers and to limit receiving audio encounter information from other speakers or other sound sources. For example, automated clinical documentation process 10 may obtain audio encounter information 106 by combining the plurality of discrete microphone elements (e.g., audio acquisition devices 202, 204, 206, 208, 210, 212, 214, 216, 218) in the microphone array (e.g., microphone array 200) with the plurality of predefined filters in such a way that signals at particular angles experience constructive interference while others experience destructive interference.

In some implementations, obtaining 506 the audio encounter information, via one or more microphone arrays, using the plurality of beams and the plurality of nulls produced by the plurality of predefined filters may include adaptively steering 514 the plurality of beams and the plurality of nulls. For example, automated clinical documentation process 10 may allow for the plurality of beams and/or the plurality of nulls to be steered toward a target speaker within the acoustic environment. Returning to the above example, suppose a patient (e.g., encounter participant 228) is speaking while moving within acoustic environment 600. Further suppose the patient (e.g., encounter participant 228) moves from approximately e.g. 45° relative to the base of microphone array 200 to approximately e.g., 35° relative to the base of microphone array 200. In this example, automated clinical documentation process 10 may adaptively steer 514 a beam (e.g., beam 220) to follow the patient (e.g., encounter participant 228) as the patient moves within acoustic environment 600. Further, suppose that while the patient (e.g., encounter participant 228) is speaking, the doctor (e.g., encounter participant 226) begins moving around within acoustic environment 600. In this example, automated clinical documentation process 10 may adaptively steer 514 a null (e.g., null 254) to follow the doctor (e.g., encounter participant 226) to limit any noise signals or audio encounter information from the doctor (e.g., encounter participant 226) while the patient (e.g., encounter participant 228) is speaking. While an example of adaptively steering one beam and one null has been provided, it will be appreciated that any number of beams and/or nulls may be adaptively steered for various purposes within the present disclosure.

In some implementations, obtaining 506 audio encounter information from particular speakers and to limit receiving audio encounter information from other speakers may include one or more of: selecting 516 one or more beams from the plurality of beams; and selecting 518 one or more nulls from the plurality of nulls. For example and as discussed above, automated clinical documentation process 10 may predefine the plurality of filters to produce the plurality of beams and/or the plurality of nulls based upon, at least in part, information associated with the acoustic environment. Referring again to FIG. 4, these actions may be generally performed by or associated with acoustic beamforming module 402. In this manner, automated clinical documentation process 10 may provide the predefined filters to beam and null selection module 508. As will be discussed in greater detail below, beam and null selection module 508 may be configured to select 516 one or more beams from the plurality of beams and/or select 518 one or more nulls from the plurality of nulls for various situations using the plurality of predefined filters.

For example and as discussed above, suppose the patient (e.g., encounter participant 228) begins speaking. Automated clinical documentation process 10 may detect the patient's audio encounter information and may select 516 one or more beams (e.g., beam 220) to receive audio encounter information from the patient (e.g., encounter participant 228). Additionally, automated clinical documentation process 10 may detect speech from another participant (e.g., participant 230). In one example, automated clinical documentation process 10 may select 516 one or more beams (e.g., beam 224) to receive audio encounter information from patient 230 or may select 518 one or more nulls (e.g., null 256) to limit receiving audio encounter information from participant 230. In this manner, automated clinical documentation process 10 may select, from the beams and nulls produced by the predefined plurality of filters, which beams and nulls to utilize when audio encounter information is detected from particular speakers.

Figure 8:
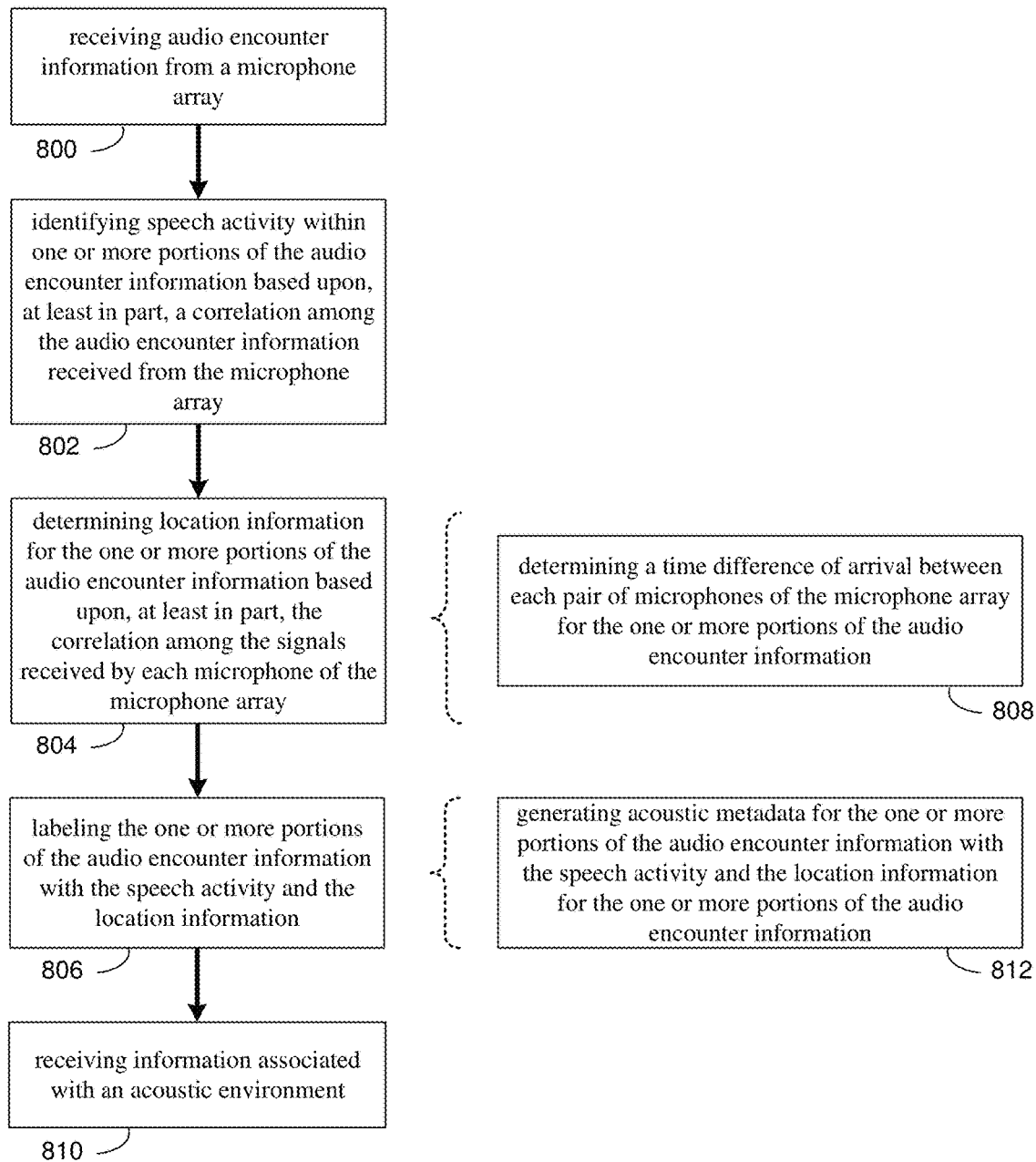
FIG. 8 is a flow chart of one implementation of the automated clinical documentation process of FIG. 1.
Figure 9:
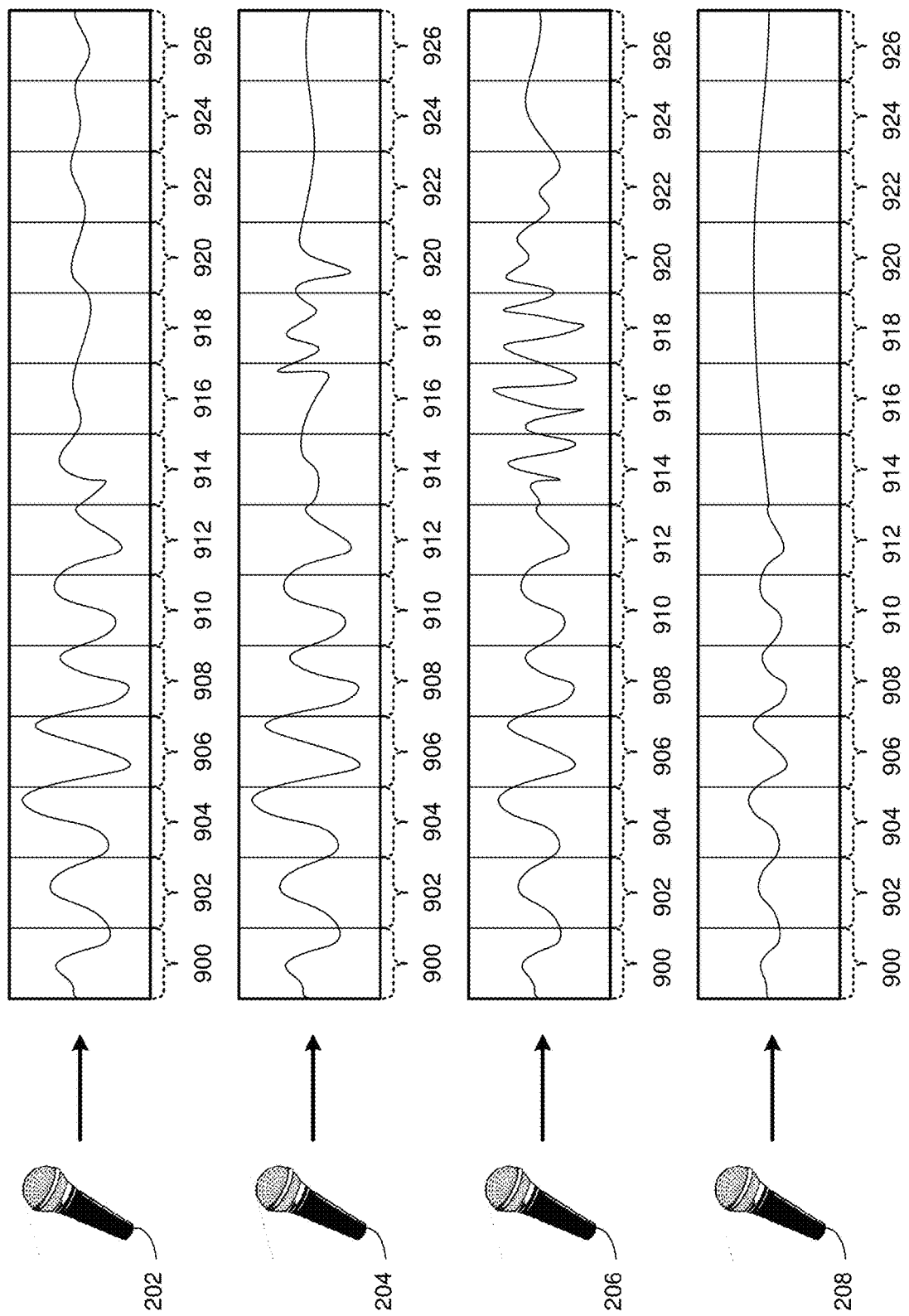
FIGS. 9-10 are diagrammatic views of audio encounter information received by various microphones of a microphone array according to various implementations of the automated clinical documentation process of FIG. 1.
Figure 10:
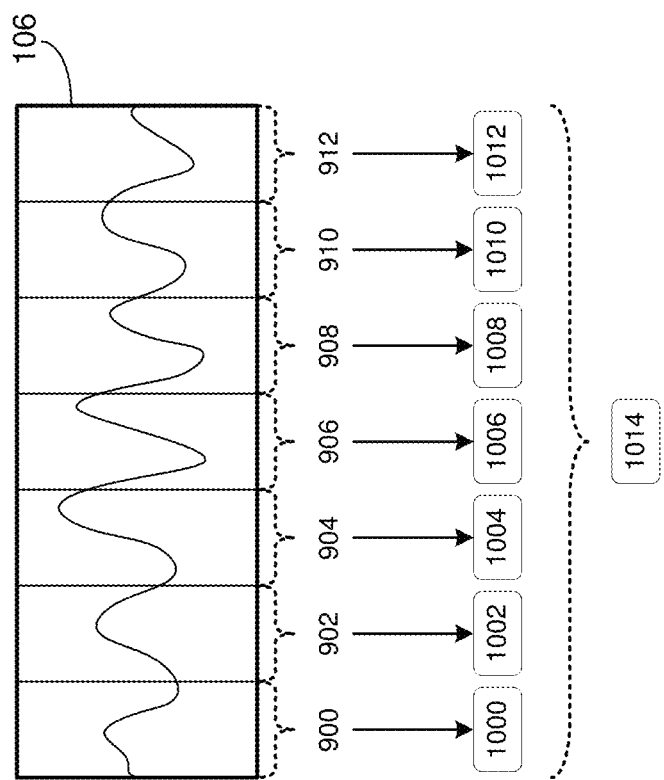
Figure 11:
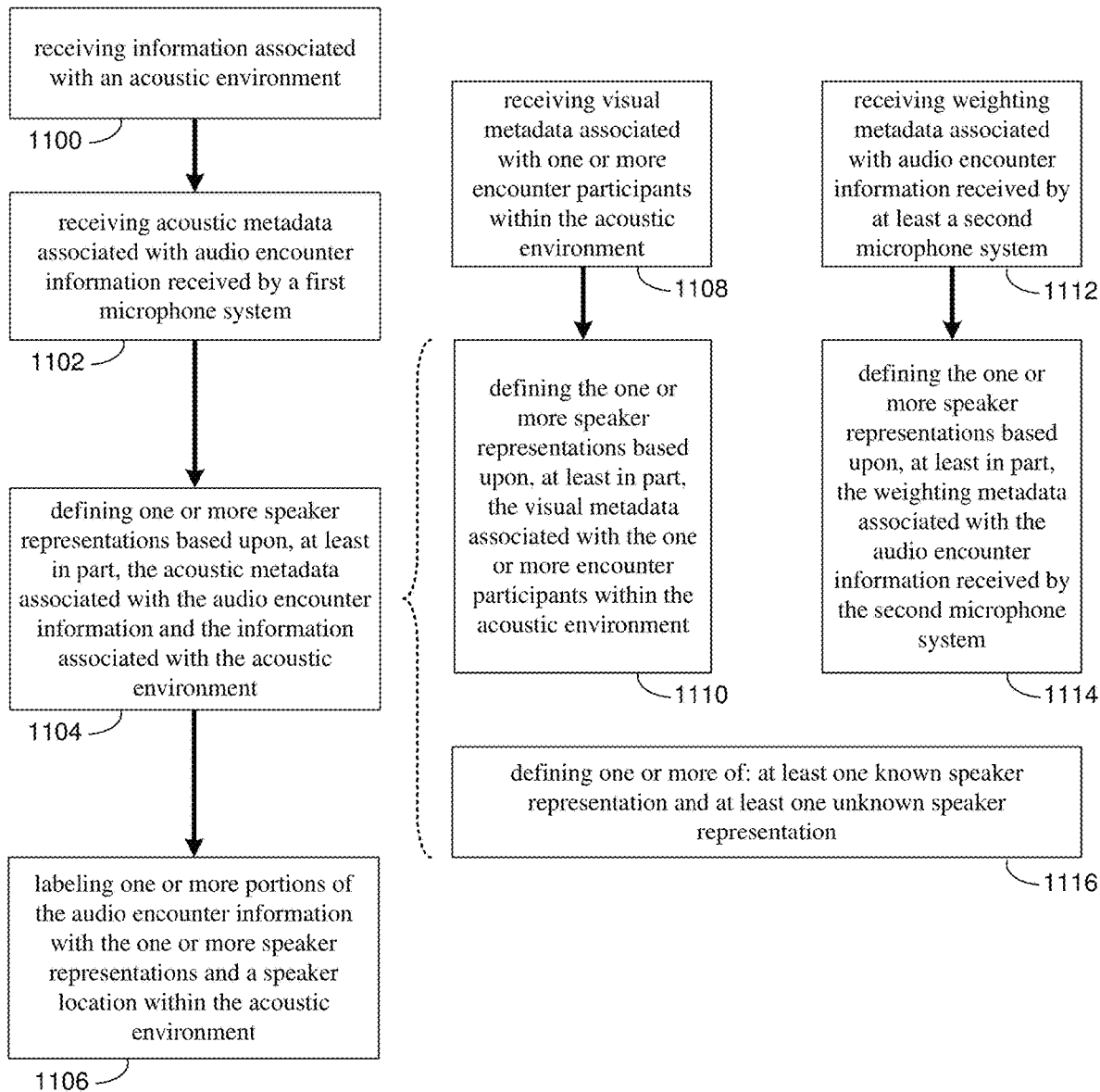
FIG. 11 is a flow chart of one implementation of the automated clinical documentation process of FIG. 1.

Referring also at least to FIGS. 8-10, automated clinical documentation process 10 may receive 800 audio encounter information from a microphone array. Speech activity within one or more portions of the audio encounter information may be identified 802 based upon, at least in part, a correlation among the audio encounter information received from the microphone array. Location information for the one or more portions of the audio encounter information may be determined 804 based upon, at least in part, the correlation among the signals received by each microphone of the microphone array. The one or more portions of the audio encounter information may be labeled 806 with the speech activity and the location information.

In some implementations, automated clinical documentation process 10 may receive 800 audio encounter information from a microphone array. Referring again to FIG. 4 and in some implementations, a microphone array (e.g., microphone array 200) may include a plurality of microphones (e.g., audio acquisition devices 202, 204, 206, 208, 210, 212, 214, 216, 218) configured to receive audio encounter information (e.g., audio encounter information 106). As discussed above, audio encounter information 106 may include speech signals or other signals recorded by the plurality of audio acquisition devices. In some implementations, automated clinical documentation process 10 may receive audio encounter information 106 at a voice activity detection (VAD) module (e.g., VAD module 400) and/or a sound localization module (e.g., sound localization module 406) of ACD computer system 12.

Referring also to FIG. 9, suppose automated clinical documentation process 10 receives audio encounter information 106 at a plurality of microphones (e.g., audio acquisition devices 202, 204, 206, 208) of microphone array 200. While only four audio acquisition devices are shown, it will be appreciated that this is for ease of explanation and that any number of audio acquisition devices of a microphone array may record audio encounter information within the scope of the present disclosure. In this example, suppose each microphone receives an audio signal (e.g., audio encounter information 106). Based on the orientation of each microphone, the properties of the audio signals, etc., each microphone may receive a different version of the signal. For example, audio encounter information received by microphone 202 may have distinct signal components (i.e., amplitude and phase) relative to the audio encounter information received by microphones 204, 206, and/or 208. As will be discussed in greater detail below, automated clinical documentation process 10 may utilize correlation between the audio encounter information to detect speech and to determine location information associated with audio encounter information.

In some implementations, automated clinical documentation process 10 may identify 802 speech activity within one or more portions of the audio encounter information based upon, at least in part, a correlation among the audio encounter information received by the microphone array. Referring again to the example of FIG. 9 and in some implementations, audio encounter information 106 may include a plurality of portions or frames of audio information (e.g., portions 900, 902, 904, 906, 908, 910, 912, 914, 916, 918, 920, 922, 924, 926). While an example with e.g., 14 portions of audio encounter information 106 have been described, it will be appreciated that this is for example purposes only and that audio encounter information 106 may include or be defined as any number of portions within the scope of the present disclosure. In one example, each portion or frame may represent audio encounter information 106 over a predefined amount of time (e.g., 20 milliseconds).

In some implementations, automated clinical documentation process 10 may determine a correlation among the audio encounter information received by microphone array 200. For example, automated clinical documentation process 10 may compare the one or more portions (e.g., portions 900, 902, 904, 906, 908, 910, 912, 914, 916, 918, 920, 922, 924, 926) of audio encounter information 106 to determine a degree of correlation between the audio encounter information present in each portion across the plurality of microphones of the microphone array. In some implementations, automated clinical documentation process 10 may perform various cross-correlation processes known in the art to determine a degree of similarity between the one or more portions (e.g., portions 900, 902, 904, 906, 908, 910, 912, 914, 916, 918, 920, 922, 924, 926) of audio encounter information 106 across the plurality of microphones of microphone array 200.

For example, suppose automated clinical documentation process 10 receives just ambient noise (i.e., no speech and no directional noise sources). Automated clinical documentation process 10 may determine that the spectrum observed in each microphone channel is different (i.e. uncorrelated at each microphone). However, suppose automated clinical documentation process 10 receives a speech or other 'directional' signal within the audio encounter information. In this example, automated clinical documentation process 10 may determine that one or more portions of the audio encounter information (e.g., the portions of audio encounter information with speech components) are highly correlated at each microphone in the microphone array.

In some implementations, automated clinical documentation process 10 may identify 802 speech activity within one or more portions of the audio encounter information based upon, at least in part, determining a threshold amount or degree of correlation among the audio encounter information received from the microphone array. For example and as discussed above, various thresholds may be defined (e.g., user-defined, default thresholds, automatically defined via automated clinical documentation process 10, etc.) to determine when portions of audio encounter information are sufficiently correlated. Accordingly, in response to determining at least a threshold degree of correlation among the portions of audio encounter information across the plurality of microphones, automated clinical documentation process 10 may determine or identify speech activity within the one or more portions of the audio encounter information. In combination with determining a threshold correlation among the portions of audio encounter information, automated clinical documentation process 10 may identify speech activity using other approaches known in the art for voice activity detection (VAD) such as filtering, noise reduction, the application of classification rules, etc. In this manner, conventional VAD techniques may be used in combination with the determination of a threshold correlation among the one or more portions of the audio encounter information to identify 802 speech activity within the one or more portions of the audio encounter information.

Referring again to the example of FIG. 9, suppose automated clinical documentation process 10 determines at least a threshold amount or degree of correlation among portions 900, 902, 904, 906, 908, 910, 912 of audio encounter information 106 across microphones 202, 204, 206, 208 and a lack of correlation among portions 914, 916, 918, 920, 922, 924, 926 of audio encounter information 106. In this example, automated clinical documentation process 10 may identify 802 speech activity within portions 900, 902, 904, 906, 908, 910, 912 of audio encounter information 106 based upon, at least in part, a threshold on the correlation among portions 900, 902, 904, 906, 908, 910, 912 of audio encounter information 106. In some implementations, identifying 802 speech activity within the one or more portions of the audio encounter information may include generating timestamps indicating portions of audio encounter information 106 that include speech activity (e.g., start and end times for each portion). In some implementations, automated clinical documentation process 10 may generate a vector of start and end times for each portion with detected speech activity. In some implementations and as will discussed in greater detail below, automated clinical documentation process 10 may label speech activity as a time domain label (i.e., a set of samples of the signal include or are speech) or as a set of frequency domain labels (i.e., a vector that gives the likelihood that a particular frequency bin in a certain time frame includes or is speech).

In some implementations, automated clinical documentation process 10 may determine 804 location information for the one or more portions of the audio encounter information based upon, at least in part, the correlation among the signals received by each microphone of the microphone array. Location information may generally include a relative location or position of the origin of audio encounter information within an acoustic environment. For example, automated clinical documentation process 10 may determine 804 location information associated with the origin of a signal received by microphone array 200. Referring again to the FIG. 6 and in some implementations, automated clinical documentation process 10 may receive audio encounter information from various sources (e.g., encounter participants 226, 228, 230; noise sources 244, 250; etc.). In some implementations, automated clinical documentation process 10 may utilize information associated with the microphone array (e.g., the spacing between microphones of the microphone array; the orientation of the microphones within the microphone array; etc.) to determine 804 location information associated with the audio encounter information received by the microphone array.

As discussed above and in some implementations, automated clinical documentation process 10 may determine a correlation among the audio encounter information received from microphone array 200. For example, automated clinical documentation process 10 may compare the one or more portions (e.g., portions 900, 902, 904, 906, 908, 910, 912, 914, 916, 918, 920, 922, 924, 926) of audio encounter information 106 received from the various microphones of microphone array 200 to determine a degree of correlation between the audio encounter information present in each portion across the plurality of microphones of the microphone array.

In some implementations, determining 804 the location information for the one or more portions of the audio encounter information may include determining 808 a time difference of arrival between each pair of microphones of the microphone array for the one or more portions of the audio encounter information. As is known in the art, a time difference of arrival (TDOA) between a pair of microphones may include locating a signal origin based upon, at least in part, the different arrival times of the signal at various receivers. In some implementations, automated clinical documentation process 10 may determine 808 the time difference of arrival (TDOA) between each pair of microphones for the one or more portions of the audio encounter information based upon, at least in part, the correlation among the audio encounter information received by the microphone array.

For example and in some implementations, a highly correlated signal (e.g., signal with at least a threshold degree of correlation) may allow for accurate determination of the time difference between microphones. As discussed above, suppose automated clinical documentation process 10 receives just ambient noise (i.e., no speech and no directional noise sources). Automated clinical documentation process 10 may determine that the spectrum observed in each microphone channel will be different (i.e. uncorrelated at each microphone). Accordingly, the time differences between pairs of microphones may be difficult to determine and/or may be inaccurate based upon the lack of correlation among the microphone channels of the microphone array. However, suppose automated clinical documentation process 10 receives a speech or other 'directional' signal within audio encounter information. In this example, automated clinical documentation process 10 may determine that one or more portions of the audio encounter information (e.g., the portions of audio encounter information with speech components) are highly correlated at each microphone in the microphone array. Accordingly, automated clinical documentation process 10 may more accurately determine the time difference of arrival between pairs of microphones using the highly correlated audio encounter information across the microphone channels of the microphone array.

In some implementations, identifying 802 the speech activity and determining 804 the location information may be performed jointly for the one or more portions of the audio encounter information. For example and as discussed above, correlation among portions of audio encounter information may identify the presence of speech activity within the one or more portions of the audio encounter information received by a microphone array. In addition and as discussed above, correlation among portions of audio encounter information may allow for a more accurate determination of location information (e.g., time difference of arrival) between pairs of microphones of the microphone array. Accordingly, automated clinical documentation process 10 may determine a correlation between the audio encounter information across the microphones or microphone channels of the microphone array and may utilize the determined correlation (e.g., by comparing the correlation to a threshold for speech activity detection and a threshold for time difference of arrival determination) to identify 802 speech activity within the one or more audio portions and to determine 804 the time difference of arrival between microphone pairs jointly.

In some implementations, jointly identifying 802 the speech activity and determining 804 the location information for the one or more portions of the audio encounter information may be performed using a machine learning model. In some implementations, automated clinical documentation process 10 may train a machine learning model to "learn" how to jointly identify speech activity and determine location information for the one or more portions of the audio encounter information. As is known in the art, a machine learning model may generally include an algorithm or combination of algorithms that has been trained to recognize certain types of patterns. For example, machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

Accordingly, automated clinical documentation process 10 may utilize a machine learning model (e.g., machine learning model 420) to identify speech activity within and location information for the one or more portions of the audio encounter information. For example, automated clinical documentation process 10 may provide time domain waveform data or frequency domain features as input to machine learning model 420. In some implementations, the phase spectrum features may provide spatial information for identifying speech activity and location information for the one or more portions of the audio encounter information.

For example, automated clinical documentation process 10 may provide training data associated with various portions of audio encounter information pre-labeled with speech activity information and/or location information to machine learning model 420. Automated clinical documentation process 10 may train machine learning model 420 to identify 802 speech activity and to determine 804 location information for the one or more portions of the audio encounter information based upon, at least in part, a degree of correlation among the portions of the audio encounter information and the training data. In this manner, machine learning model 420 may be configured to learn how correlation between portions of audio encounter information maps to speech activity within and accurate location information for the portions of the audio encounter information. Accordingly, and as shown in FIG. 4, automated clinical documentation process 10 may implement VAD module 400 and sound localization module 406 with machine learning model 420.

In some implementations, automated clinical documentation process 10 may receive 810 information associated with an acoustic environment. As discussed above, an acoustic environment may represent the layout and acoustic properties of a room or other space where multiple microphone systems may be deployed. For example, information associated with the acoustic environment may describe the type/dimensions of a room, the activity zones in the room where the participants operate, the acoustic properties of the room (e.g., the types of noise expected, range of reverberation, etc.), position of the microphone system(s) within the acoustic environment, etc. In some implementations, automated clinical documentation process 10 may provide a user interface to receive information associated with the acoustic environment. Accordingly, a user and/or automated clinical documentation process 10 may provide the information associated with an acoustic environment via the user interface. However, it will be appreciated that the information associated with the acoustic environment may be received in various ways (e.g., default information for a default acoustic environment, automatically defined by automated clinical documentation process 10, etc.).

In some implementations, the information associated with the acoustic environment may indicate one or more target speaker locations within the acoustic environment. Referring again to FIG. 6 and in some implementations, suppose that acoustic environment 600 includes one or more encounter participants (e.g., encounter participants 226, 228, 230) of the above-described patient encounter. As described above, examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

In some implementations, automated clinical documentation process 10 may receive 810 information associated with acoustic environment 600 that may indicate locations within acoustic environment 600 where encounter participants 226, 228, 230 may be positioned. In some implementations, the information associated with acoustic environment 600 may indicate locations within acoustic environment where the one or more target speakers are likely to be when speaking. For example, suppose automated clinical documentation process 10 determines that an examination table is positioned at approximately e.g., 45° from the base of microphone array 200. In this example, automated clinical documentation process 10 may determine that a patient is most likely to speak while sitting on or near the examination table at approximately 45° from the base of microphone array 200. Further suppose that automated clinical documentation process 10 determines that a doctor's desk is positioned at approximately e.g., 90° from the base of microphone array 200. In this example, automated clinical documentation process 10 may determine that a doctor is most likely to speak while sitting on or near the desk at approximately 90° from the base of microphone array 200. Additionally, suppose automated clinical documentation process 10 determines that a waiting area is positioned at approximately e.g., 120° from the base of microphone array 200. In this example, automated clinical documentation process 10 may determine that other patients or other third parties are most likely to speak from at approximately 120° from the base of microphone array 200. While three examples of relative locations for target speakers within an acoustic environment have been provided, it will be appreciated that the information associated with the acoustic environment may include any number of target speaker locations or probability-based target speaker locations for any number of target speakers within the scope of the present disclosure.

In some implementations, identifying 802 the speech activity within the one or more portions of the audio encounter information may be based upon, at least in part, the location information for the one or more portions of the audio encounter information and the information associated with the acoustic environment. For example, automated clinical documentation process 10 may utilize the information associated with the acoustic environment to more accurately identify speech activity within the one or more portions of the audio encounter information. In one example, suppose that automated clinical documentation process 10 receives information associated with the acoustic environment that indicates locations within the acoustic environment where speakers are likely to be. In this example, automated clinical documentation process 10 may, based upon the location information for the one or more portions of the audio encounter information, determine whether the one or more portions of the audio encounter information are within the potential speaker locations defined by the acoustic environment information. In response to determining that the one or more portions of the audio encounter information originate from a potential speaker location within the acoustic environment, automated clinical documentation process 10 may determine a higher probability that the one or more portions of the audio encounter information include speech activity. Accordingly, automated clinical documentation process 10 may utilize the location information and the acoustic environment information to identify 802 speech activity within the one or more portions of the audio encounter information.

In some implementations, automated clinical documentation process 10 may label 806 the one or more portions of the audio encounter information with the speech activity and the location information. Labeling one or more portions of the audio encounter information with the speech activity and the location information may generally include generating metadata for the one or more portions of the audio encounter information with the speech activity and location information associated with each respective portion of the audio encounter information. Referring also to FIG. 10 and in some implementations, automated clinical documentation process 10 may label 806 portions 900, 902, 904, 906, 908, 910, 912 with the speech activity and location information associated with each respective portion by generating acoustic metadata for each portion of audio encounter information 106 (e.g., acoustic metadata 1000, 1002, 1004, 1006, 1008, 1010, 1012). In some implementations, the acoustic metadata associated with the audio encounter information may include the speech activity and the location information associated with the audio encounter information. In some implementations, automated clinical documentation process 10 may generate acoustic metadata 1000, 1002, 1004, 1006, 1008, 1010, 1012 that identifies portions of audio encounter information 106 that includes speech activity (e.g., portions 900, 902, 904, 906, 908, 910, 912). In one example, automated clinical documentation process 10 may generate acoustic metadata with timestamps indicating portions of audio encounter information 106 that include speech activity (e.g., start and end times for each portion). In some implementations, automated clinical documentation process 10 may label 806 speech activity as a time domain label (i.e., a set of samples of the signal include or are speech) or as a set of frequency domain labels (i.e., a vector that gives the likelihood that a particular frequency bin in a certain time frame includes or is speech).

Referring again to FIG. 4 and as will be discussed in greater detail below, automated clinical documentation process 10 may provide the acoustic metadata (e.g., acoustic metadata 1014) to speaker identification and tracking module 404 to identify a speaker from the audio encounter information and/or to track the position of a speaker within an acoustic environment based upon, at least in part, acoustic metadata 1014.

Referring also at least to FIGS. 11-14, automated clinical documentation process 10 may receive 1100 information associated with an acoustic environment. Acoustic metadata associated with audio encounter information received by a first microphone system may be received 1102. One or more speaker representations may be defined 1104 based upon, at least in part, the acoustic metadata associated with the audio encounter information and the information associated with the acoustic environment. One or more portions of the audio encounter information may be labeled 1106 with the one or more speaker representations and a speaker location within the acoustic environment.

In some implementations, automated clinical documentation process 10 may receive 1100 information associated with an acoustic environment. As discussed above, an acoustic environment may represent the layout and acoustic properties of a room or other space where multiple microphone systems may be deployed. For example, information associated with the acoustic environment may describe the type/dimensions of a room, the activity zones in the room where the participants operate, the acoustic properties of the room (e.g., the types of noise expected, range of reverberation, etc.), position of the microphone system(s) within the acoustic environment, etc. In some implementations, automated clinical documentation process 10 may provide a user interface to receive information associated with the acoustic environment. Accordingly, a user and/or automated clinical documentation process 10 may provide the information associated with an acoustic environment via the user interface. However, it will be appreciated that the information associated with the acoustic environment may be received in various ways (e.g., default information for a default acoustic environment, automatically defined by automated clinical documentation process 10, etc.).

In some implementations, the information associated with the acoustic environment may indicate one or more target speaker locations within the acoustic environment. Referring again to FIG. 6 and in some implementations, suppose that acoustic environment 600 includes one or more encounter participants (e.g., encounter participants 226, 228, 230) of the above-described patient encounter. As described above, examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

In some implementations, automated clinical documentation process 10 may receive 1100 information associated with acoustic environment 600 that may indicate locations within acoustic environment 600 where encounter participants 226, 228, 230 may be positioned. In some implementations, the information associated with acoustic environment 600 may indicate locations within acoustic environment where the one or more target speakers are likely to be when speaking. For example, suppose automated clinical documentation process 10 determines that an examination table is positioned at approximately e.g., 45° from the base of microphone array 200. In this example, automated clinical documentation process 10 may determine that a patient is most likely to speak while sitting on or near the examination table at approximately 45° from the base of microphone array 200. Further suppose that automated clinical documentation process 10 determines that a doctor's desk is positioned at approximately e.g., 90° from the base of microphone array 200. In this example, automated clinical documentation process 10 may determine that a doctor is most likely to speak while sitting on or near the desk at approximately 90° from the base of microphone array 200.

Additionally, suppose automated clinical documentation process 10 determines that a waiting area is positioned at approximately e.g., 120° from the base of microphone array 200. In this example, automated clinical documentation process 10 may determine that other patients or other third parties are most likely to speak from at approximately 120° from the base of microphone array 200. While three examples of relative locations for target speakers within an acoustic environment have been provided, it will be appreciated that the information associated with the acoustic environment may include any number of target speaker locations or probability-based target speaker locations for any number of target speakers within the scope of the present disclosure.

In some implementations, automated clinical documentation process 10 may receive 1102 acoustic metadata associated with audio encounter information received by a first microphone system. Referring again to FIG. 4 and in some implementations, VAD module 400 and sound localization module 406 may generate acoustic metadata associated with audio encounter information. For example and in some implementations, the acoustic metadata associated with the audio encounter information may include speech activity information and signal location information associated with the audio encounter information. As discussed above and in some implementations, automated clinical documentation process 10 may identify portions of the audio encounter information (e.g., audio encounter information 106) with speech components. Automated clinical documentation process 10 may associate or label the portions of audio encounter information 106 as having speech activity. In some implementations, automated clinical documentation process 10 may generate acoustic metadata that identifies portions of audio encounter information 106 that includes speech activity.

Figure 12:
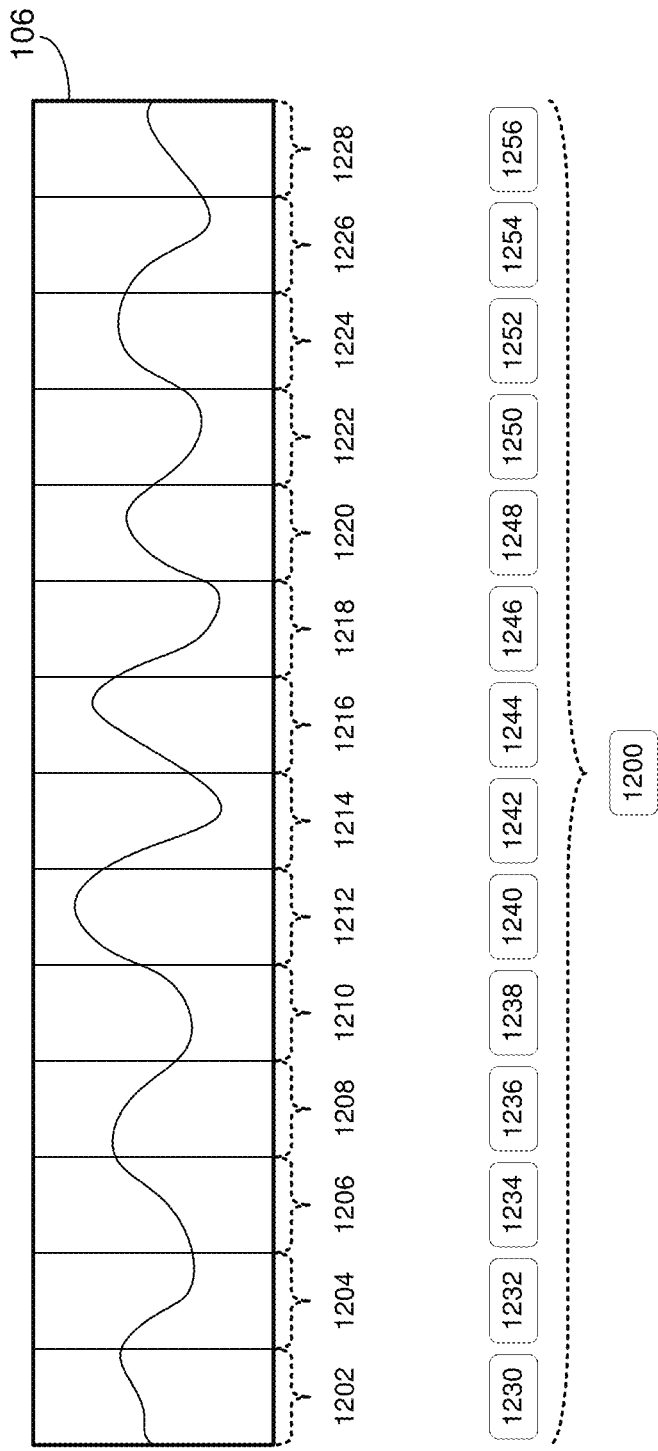
FIG. 12 is a diagrammatic view of audio encounter information received by various microphones of a microphone array according to various implementations of the automated clinical documentation process of FIG. 1.

In one example, automated clinical documentation process 10 may generate timestamps indicating portions of audio encounter information 106 that include speech activity (e.g., start and end times for each portion). Referring also to FIG. 12, automated clinical documentation process 10 may receive acoustic metadata 1200 for one or more portions of audio encounter information 106 (e.g., portions 1202, 1204, 1206, 1208, 1210, 1212, 1214, 1216, 1218, 1220, 1222, 1224, 1226, 1228). As discussed above, automated clinical documentation process 10 may generate acoustic metadata with speech activity and signal location information associated with each portion of the audio encounter information (e.g., represented in FIG. 12 as acoustic metadata 1230, 1232, 1234, 1236, 1238, 1240, 1242, 1244, 1246, 1248, 1250, 1252, 1254, 1256 for portions 1202, 1204, 1206, 1208, 1210, 1212, 1214, 1216, 1218, 1220, 1222, 1224, 1226, 1228, respectively) of audio encounter information 106).

Additionally, automated clinical documentation process 10 may determine location information for audio encounter information 106. For example, automated clinical documentation process 10 may determine spatial information from the microphone array (e.g., time difference of arrival (TDOA) between the microphones). As is known in the art, once a signal is received at two reference points, the difference in arrival time may be used to calculate the difference in distances between the target and the two reference points. In this example, automated clinical documentation process 10 may determine the time difference of arrival (TDOA) between microphones of a microphone array. In some implementations, automated clinical documentation process 10 may generate acoustic metadata with the TDOA for a particular microphone array.

In some implementations, automated clinical documentation process 10 may define 1104 one or more speaker representations based upon, at least in part, the acoustic metadata associated with the audio encounter information and the information associated with the acoustic environment. A speaker representation may generally include a cluster of data associated with a unique speaker within an acoustic environment. For example, automated clinical documentation process 10 may cluster spatial information and spectral information into separate speaker representations to account for the combination of spatial and spectral data that reference unique speakers within an acoustic environment.

Referring again to FIG. 6 and in some implementations, suppose automated clinical documentation process 10 receives 1100 information associated with acoustic environment 600 that may indicate locations within acoustic environment 600 where encounter participants 226, 228, 230 may be positioned. Further suppose that automated clinical documentation process 10 receives 1102 acoustic metadata (e.g., acoustic metadata 1200) associated with audio encounter information 106 received by microphone array 200. In this example, suppose that acoustic metadata 1200 includes spatial information (e.g., location information for audio encounter information 106) and spectral information (e.g., speech activity information). In some implementations, the spectral information may include acoustic features (e.g., Mel frequency cepstral coefficients (MFCCs)) associated with particular speakers (e.g., encounter participants 226, 228, 230).

Figure 13:
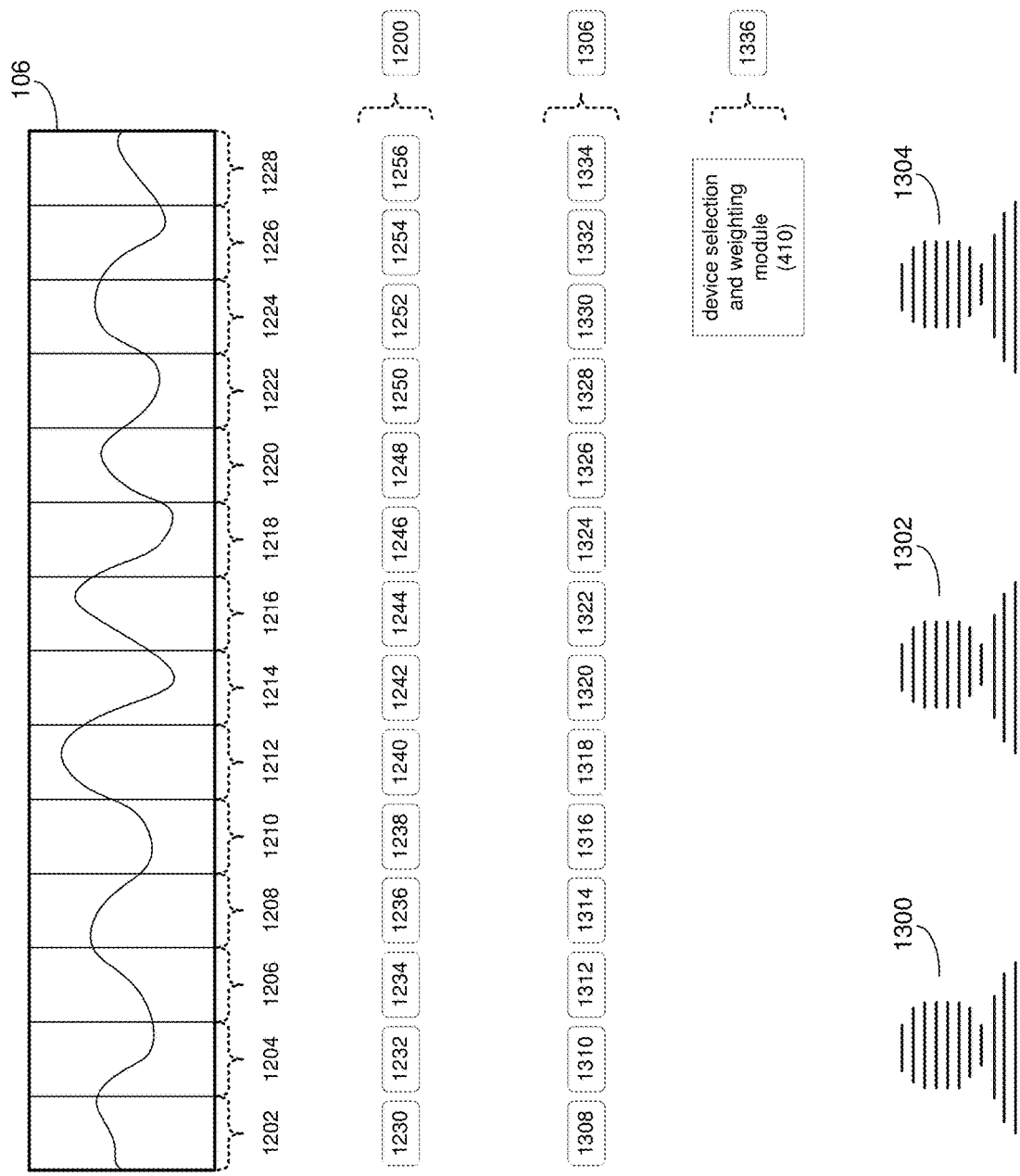
FIG. 13 is a diagrammatic view of a plurality of speaker representations generated according to one implementation of the automated clinical documentation process of FIG. 1.

Referring also to FIG. 13 and in some implementations, automated clinical documentation process 10 may define 1104 speaker representations for encounter participants 226, 228, 230 based upon, at least in part, the acoustic metadata associated with the audio encounter information and the information associated with the acoustic environment. For example, automated clinical documentation process 10 may use a dynamic model of speaker movements and the information associated with the acoustic environment to cluster the spatial information (e.g., TDOA) and spectral information (e.g., acoustic features like MFCCs) into separate speaker representations (e.g., speaker representation 1300 for encounter participant 226; speaker representation 1302 for encounter participant 228; and speaker representation 1304 for encounter participant 230). While the above example includes defining e.g., three speaker representations, it will be appreciated that any number of speaker representations may be defined by automated clinical documentation process 10 within the scope of the present disclosure.

In some implementations, automated clinical documentation process 10 may receive 1108 visual metadata associated with one or more encounter participants within the acoustic environment. For example, automated clinical documentation process 10 may be configured to track the movement and/or interaction of humanoid shapes within the monitored space (e.g., acoustic environment 600) during the patient encounter (e.g., a visit to a doctor's office). Accordingly and referring again to FIG. 2, automated clinical documentation process 10 may process the machine vision encounter information (e.g., machine vision encounter information 102) to identify one or more humanoid shapes. As discussed above, examples of machine vision system 100 generally (and ACD client electronic device 34 specifically) may include but are not limited to one or more of an RGB imaging system, an infrared imaging system, an ultraviolet imaging system, a laser imaging system, a SONAR imaging system, a RADAR imaging system, and a thermal imaging system.

When ACD client electronic device 34 includes a visible light imaging system (e.g., an RGB imaging system), ACD client electronic device 34 may be configured to monitor various objects within acoustic environment 600 by recording motion video in the visible light spectrum of these various objects. When ACD client electronic device 34 includes an invisible light imaging systems (e.g., a laser imaging system, an infrared imaging system and/or an ultraviolet imaging system), ACD client electronic device 34 may be configured to monitor various objects within acoustic environment 600 by recording motion video in the invisible light spectrum of these various objects. When ACD client electronic device 34 includes an X-ray imaging system, ACD client electronic device 34 may be configured to monitor various objects within acoustic environment 600 by recording energy in the X-ray spectrum of these various objects. When ACD client electronic device 34 includes a SONAR imaging system, ACD client electronic device 34 may be configured to monitor various objects within acoustic environment 600 by transmitting soundwaves that may be reflected off of these various objects. When ACD client electronic device 34 includes a RADAR imaging system, ACD client electronic device 34 may be configured to monitor various objects within acoustic environment 600 by transmitting radio waves that may be reflected off of these various objects. When ACD client electronic device 34 includes a thermal imaging system, ACD client electronic device 34 may be configured to monitor various objects within acoustic environment 600 by tracking the thermal energy of these various objects.

As discussed above, ACD computer system 12 may be configured to access one or more datasources 118 (e.g., plurality of individual datasources 120, 122, 124, 126, 128), wherein examples of which may include but are not limited to one or more of a user profile datasource, a voice print datasource, a voice characteristics datasource (e.g., for adapting the automated speech recognition models), a face print datasource, a humanoid shape datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

Accordingly and when processing the machine vision encounter information (e.g., machine vision encounter information 102) to identify one or more humanoid shapes, automated clinical documentation process 10 may be configured to compare the humanoid shapes defined within one or more datasources 118 to potential humanoid shapes within the machine vision encounter information (e.g., machine vision encounter information 102).

When processing the machine vision encounter information (e.g., machine vision encounter information 102) to identify one or more humanoid shapes, automated clinical documentation process 10 may track the movement of the one or more humanoid shapes within the monitored space (e.g., acoustic environment 600). For example and when tracking the movement of the one or more humanoid shapes within acoustic environment 600, automated clinical documentation process 10 may add a new humanoid shape to the one or more humanoid shapes when the new humanoid shape enters the monitored space (e.g., acoustic environment 600) and/or may remove an existing humanoid shape from the one or more humanoid shapes when the existing humanoid shape leaves the monitored space (e.g., acoustic environment 600).

Also and when tracking the movement of the one or more humanoid shapes within acoustic environment 600, automated clinical documentation process 10 may monitor the trajectories of the various humanoid shapes within acoustic environment 600. Accordingly, assume that when leaving acoustic environment 600, encounter participant 242 walks in front of (or behind) encounter participant 226. As automated clinical documentation process 10 is monitoring the trajectories of (in this example) encounter participant 242 (who is e.g., moving from left to right) and encounter participant 226 (who is e.g., stationary), when encounter participant 242 passes in front of (or behind) encounter participant 226, the identities of these two humanoid shapes may not be confused by automated clinical documentation process 10.

Automated clinical documentation process 10 may be configured to obtain the encounter information of the patient encounter (e.g., a visit to a doctor's office), which may include machine vision encounter information 102 (in the manner described above) and/or audio encounter information 106. In some implementations, automated clinical documentation process 10 may generate visual metadata associated with machine vision encounter information 102. For example and as discussed above, automated clinical documentation process 10 may generate visual metadata 1306 indicative of the direction or position of speakers within acoustic environment 600, the number of speakers within acoustic environment 600, and/or the identity of the speakers within acoustic environment 600. As shown in the example of FIG. 13, visual metadata 1306 may be defined for each portion of audio encounter information 106 (e.g., portions 1202, 1204, 1206, 1208, 1210, 1212, 1214, 1216, 1218, 1220, 1222, 1224, 1226, 1228 of audio encounter information 106) and represented as separate visual metadata for each portion (e.g., visual metadata 1308, 1310, 1312, 1314, 1316, 1318, 1320, 1322, 1324, 1326, 1328, 1330, 1332, 1334).

In some implementations, defining 1104 the one or more speaker representations may include defining 1110 the one or more speaker representations based upon, at least in part, the visual metadata associated with the one or more encounter participants within the acoustic environment. For example and as discussed above, machine vision system 100 may detect and track location estimates for particular speaker representations by tracking the humanoid shapes within the acoustic environment. Automated clinical documentation process 10 may "fuse" the location estimates from the visual metadata with the acoustic localization information to cluster the spatial-spectral features of the visual metadata and the acoustic metadata into the plurality of speaker representations.

Referring again to the example of FIG. 6, automated clinical documentation process 10 may receive 1108 visual metadata 1306 associated with encounter participants 226, 228, 230. In this example, visual metadata 1306 may indicate the relative position of each speaker within acoustic environment 600; the number of speakers; and/or the identity of the speakers within acoustic environment 600. For example and as discussed above, machine vision system 100 may be configured to identify one or more humanoid shapes and track the movement of the one or more humanoid shapes within the acoustic environment. Automated clinical documentation process 10 may receive visual metadata 1306 associated with the identity and/or location of encounter participants 226, 228, 230. Suppose that visual metadata 1306 includes an identity of each participant (e.g., based upon, at least in part, comparing the humanoid shapes defined within one or more datasources 118 to potential humanoid shapes within the machine vision encounter information (e.g., machine vision encounter information 102)).

Further suppose that automated clinical documentation process 10 receives 1102 acoustic metadata 1200 associated with audio encounter information 106. Automated clinical documentation process 10 may define 1110 the one or more speaker representations (e.g., speaker representations 1300, 1302, 1304 for encounter participants 226, 228, 230, respectively) based upon, at least in part, visual metadata 1306 associated with encounter participants 226, 228, 230 within acoustic environment 600 and acoustic metadata 1200 associated with the audio encounter information 106. In this example, automated clinical documentation process 10 may combine the location estimates from visual metadata 1306 with the location information of acoustic metadata 1200 to cluster the spatial-spectral features of visual metadata 1306 and acoustic metadata 1200 into speaker representations 1300, 1302, 1304 for encounter participants 226, 228, 230, respectively.

In some implementations, automated clinical documentation process 10 may receive 1112 weighting metadata associated with audio encounter information received by a second microphone system. As will be discussed in greater detail below, device selection and weighting module 410 of ACD computer system 12 may be configured to weight multiple audio streams (e.g., from different microphone systems) based upon, at least in part, a signal-to-noise ratio for each audio stream, thus defining a weight for each audio stream. In some implementations, the weight may be defined for each audio stream such that the estimated speech processing system performance is maximized. For example, automated clinical documentation process 10 may train the device selection and weighting module based upon, at least in part, the signal-to-noise (SNR) ratio for each portion or frame of each audio stream. However, it will be appreciated that other metrics or properties associated with each audio stream may be utilized to select and weight each audio stream. For example, automated clinical documentation process 10 may train the device selection and weighting module based upon, at least in part, a reverberation level (e.g., a C50 ratio) for each portion or frame of each audio stream. While two examples of particular metrics that may be used to select and weight each audio stream have been provided, it will be appreciated that any metric or property may be used to select and/or weigh various audio streams within the scope of the present disclosure. In some implementations, device selection and weighting module 410 may provide a previously processed or weighted portion of the audio encounter information to define weighting for each audio stream from multiple microphone systems. In this manner, automated clinical documentation process 10 may utilize audio encounter information from multiple microphone systems when tracking and/or identifying a speaker.

In some implementations, defining 1104 the one or more speaker representations may include defining 1114 the one or more speaker representations based upon, at least in part, the weighting metadata associated with the audio encounter information received by the second microphone system. For example, automated clinical documentation process 10 may utilize weighting metadata (e.g., weighting metadata 1336) associated with audio encounter information received by a second microphone system (e.g., second microphone system 416) to help identify which speaker is speaking at a given time within the acoustic environment (e.g., acoustic environment 600).

For example, suppose that encounter participant 226 has a second microphone system (e.g., mobile electronic device 416) nearby (e.g., in a pocket). In some implementations, the second microphone system (e.g., mobile electronic device 416) may receive audio encounter information 106 from encounter participants 226, 228, 230. As will be discussed in greater detail below, automated clinical documentation process 10 may apply a weight to portions of the audio encounter information received by the first microphone system (e.g., microphone array 200) and a weight to portions of the audio encounter information received by the second microphone system (e.g., mobile electronic device 416). In some implementations, automated clinical documentation process 10 may generate weighting metadata (e.g., weighting metadata 1336) associated with the audio encounter information received by the second microphone system (e.g., mobile electronic device 416). For example, weighting metadata 1336 may indicate that, based on audio encounter information received by mobile electronic device 416, encounter participant 226 is speaking. Accordingly, automated clinical documentation process 10 may define 1114 the speaker representation for encounter participant 226 based upon, at least in part, weighting metadata 1336 associated with the audio encounter information received by the second microphone system.

In some implementations, defining 1104 the one or more speaker representations may include defining 1116 one or more of: at least one known speaker representation and at least one unknown speaker representation. For example and as discussed above, ACD computer system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource.

In some implementations, process 10 may compare the data included within the user profile (defined within the user profile datasource) to at least a portion of the audio encounter information and/or machine vision encounter information. The data included within the user profile may include voice-related data (e.g., a voice print that is defined locally within the user profile or remotely within the voice print datasource), language use patterns, user accent identifiers, user-defined macros, and user-defined shortcuts, for example. Specifically and when attempting to associate at least a portion of the audio encounter information with at least one known encounter participant, automated clinical documentation process 10 may compare one or more voice prints (defined within the voice print datasource) to one or more voices defined within the audio encounter information.

As discussed above and for this example, assume: that encounter participant 226 is a medical professional that has a voice print/profile; that encounter participant 228 is a patient that has a voice print/profile; and that encounter participant 230 is a third party (the acquaintance of encounter participant 228) and, therefore, does not have a voice print/profile. Accordingly and for this example: assume that automated clinical documentation process 10 will be successful and identify encounter participant 226 when comparing audio encounter information 106A to the various voice prints/profiles included within voice print datasource; assume that automated clinical documentation process 10 will be successful and identify encounter participant 228 when comparing audio encounter information 106B to the various voice prints/profiles included within voice print datasource; and assume that automated clinical documentation process 10 will be unsuccessful and not identify encounter participant 230 when comparing audio encounter information 106C to the various voice prints/profiles included within voice print datasource.

Accordingly and when processing the encounter information (e.g., machine vision encounter information 102 and/or audio encounter information 106), automated clinical documentation process 10 may associate audio encounter information 106A with the voice print/profile of Doctor Susan Jones and may identify encounter participant 226 as "Doctor Susan Jones". Automated clinical documentation process 10 may further associate audio encounter information 106B with the voice print/profile of Patient Paul Smith and may identify encounter participant 228 as "Patient Paul Smith". Further, automated clinical documentation process 10 may not be able to associate audio encounter information 106C with any voice prints/profiles and may identify encounter participant 230 as "Unknown Participant".

As described above, automated clinical documentation process 10 may define 1116 a known speaker representation for "Doctor Susan Jones" (e.g., speaker representation 1300 for encounter participant 226) and a known speaker representation for "Patient Paul Smith" (e.g., speaker representation 1302 for encounter participant 228) based upon, at least in part, acoustic metadata 1200 associated with audio encounter information 106 and visual metadata 1306 associated with machine vision encounter information 102. Similarly, automated clinical documentation process 10 may define an unknown speaker representation for participant 230 (e.g., speaker representation 1304 for encounter participant 230).

In some implementations, automated clinical documentation process 10 may label 1106 one or more portions of the audio encounter information with the one or more speaker representations and a speaker location within the acoustic environment. For example, labeling 1106 one or more portions of the audio encounter information with the one or more speaker representations and a speaker location within the acoustic environment may generally include associating a speaker representation and speaker location information within the acoustic environment with a particular portion (e.g., a segment or frame) of the audio encounter information. For example, automated clinical documentation process 10 may generate labels for each portion of the audio encounter information with the speaker representation and a speaker location within the acoustic environment associated with each portion.

Figure 14:
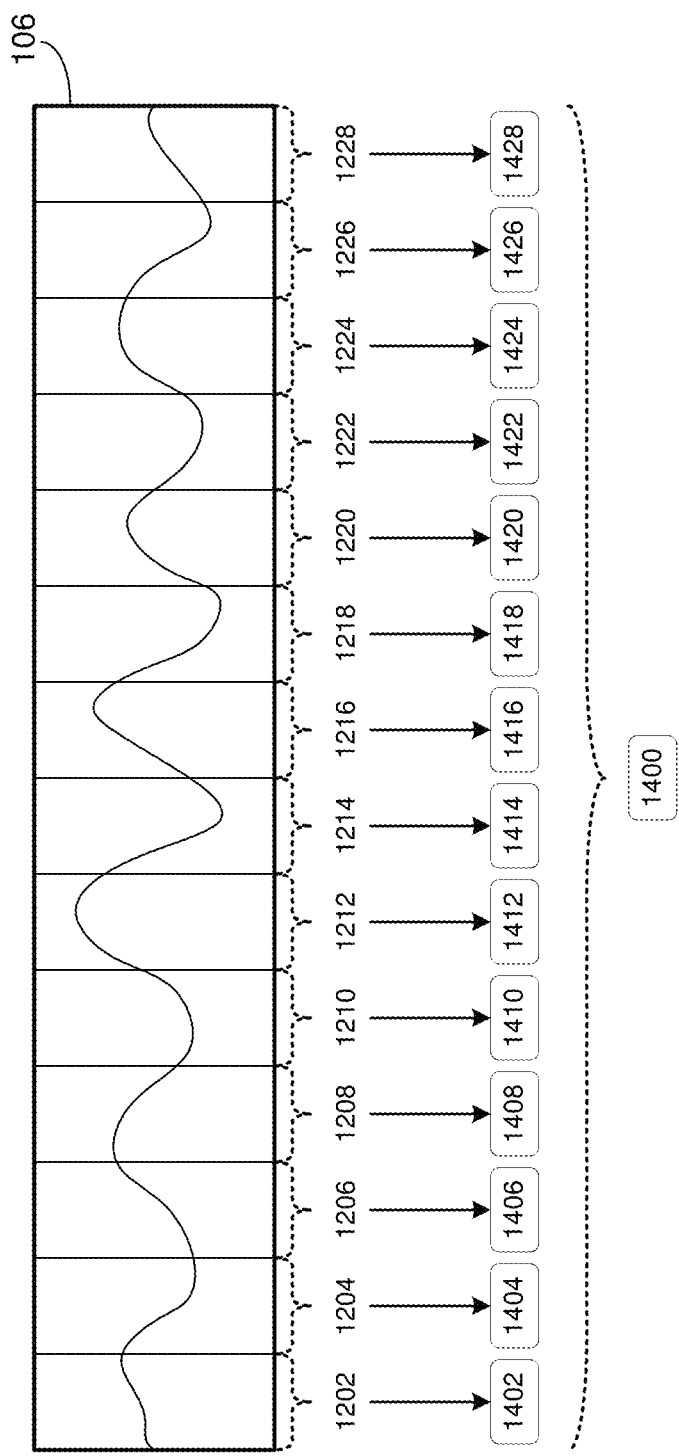
FIG. 14 is a diagrammatic view of speaker metadata generated according to various implementations of the automated clinical documentation process of FIG. 1.

Referring also to FIG. 14 and in some implementations, automated clinical documentation process 10 may label one or more portions of the audio encounter information (e.g., portions 1202, 1204, 1206, 1208, 1210, 1212, 1214, 1216, 1218, 1220, 1222, 1224, 1226, 1228 of audio encounter information 106) with the one or more speaker representations and a speaker location within the acoustic environment. For example, automated clinical documentation process 10 may, for each portion of audio encounter information 106, generate a "label" or speaker metadata 1400 (e.g., represented as speaker metadata 1402, 1404, 1406, 1408, 1410, 1412, 1414, 1416, 1418, 1420, 1422, 1424, 1426, 1428 defined for portions 1202, 1204, 1206, 1208, 1210, 1212, 1214, 1216, 1218, 1220, 1222, 1224, 1226, 1228, respectively) with the speaker representation and speaker location information associated with that portion of audio encounter information 106.

Continuing with the above example, suppose portions 1202, 1204, 1206, 1208, 1210 include speech from encounter participant 226; portions 1212, 1214, 1216, 1218, 1220 include speech from encounter participant 228; and that portions 1222, 1224, 1226, 1228 include speech from encounter participant 230. In this example, automated clinical documentation process 10 may label portions 1202, 1204, 1206, 1208, 1210 with speaker representation 1300 and a speaker location within the acoustic environment associated with speaker 226 during the associated portion of the audio encounter information; may label portions 1212, 1214, 1216, 1218, 1220 with speaker representation 1302 and a speaker location within the acoustic environment associated with encounter participant 228 during the associated portions of the audio encounter information; and may label portions 1222, 1224, 1226, 1228 with speaker representation 1304 and a speaker location within the acoustic environment associated with encounter participant 230 during the associated portions of the audio encounter information. As will be discussed in greater detail below, speaker metadata 1400 may be provided to a beam and null selection module (e.g., beam and null selection module 406) of ACD computing system 12 and may allow for the selection and/or combination of particular beams and/or nulls based upon, at least in part, the speaker representation and speaker location defined within speaker metadata 1400.

Figure 15:
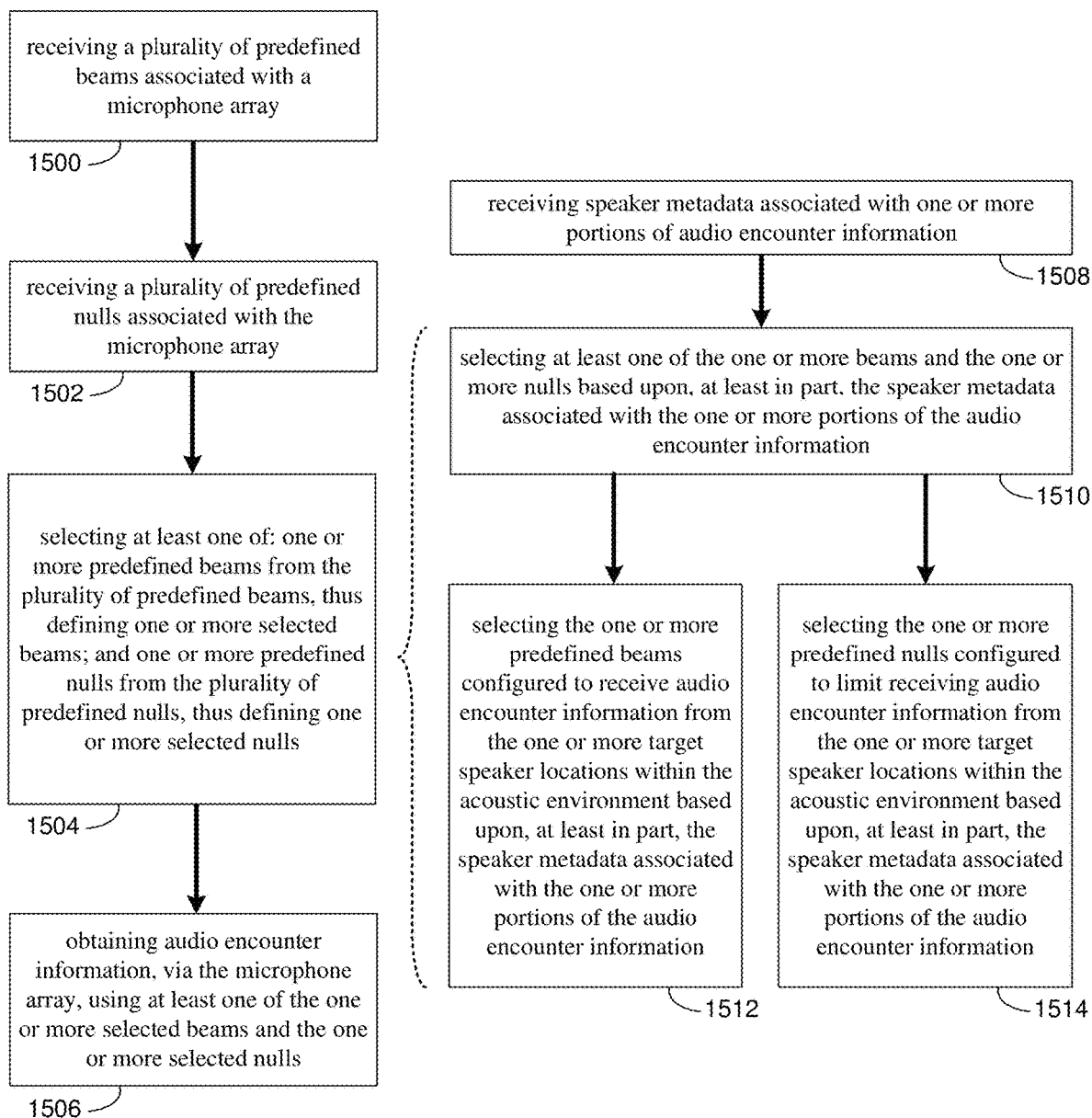
FIG. 15 is a flow chart of one implementation of the automated clinical documentation process of FIG. 1.
Figure 16:
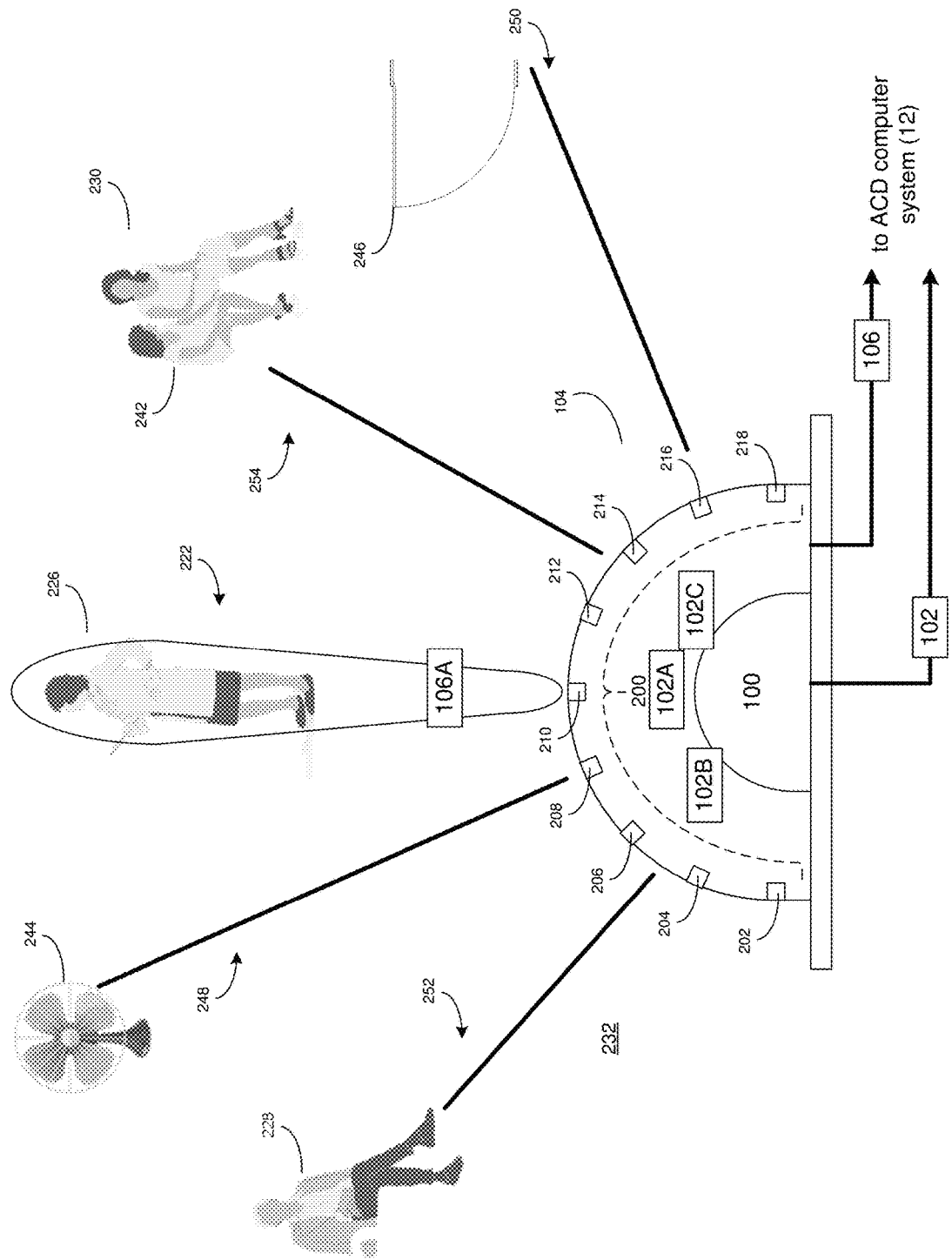
FIG. 16 is a diagrammatic view of a modular ACD system according to one implementation of the automated clinical documentation process of FIG. 1.
Figure 17:
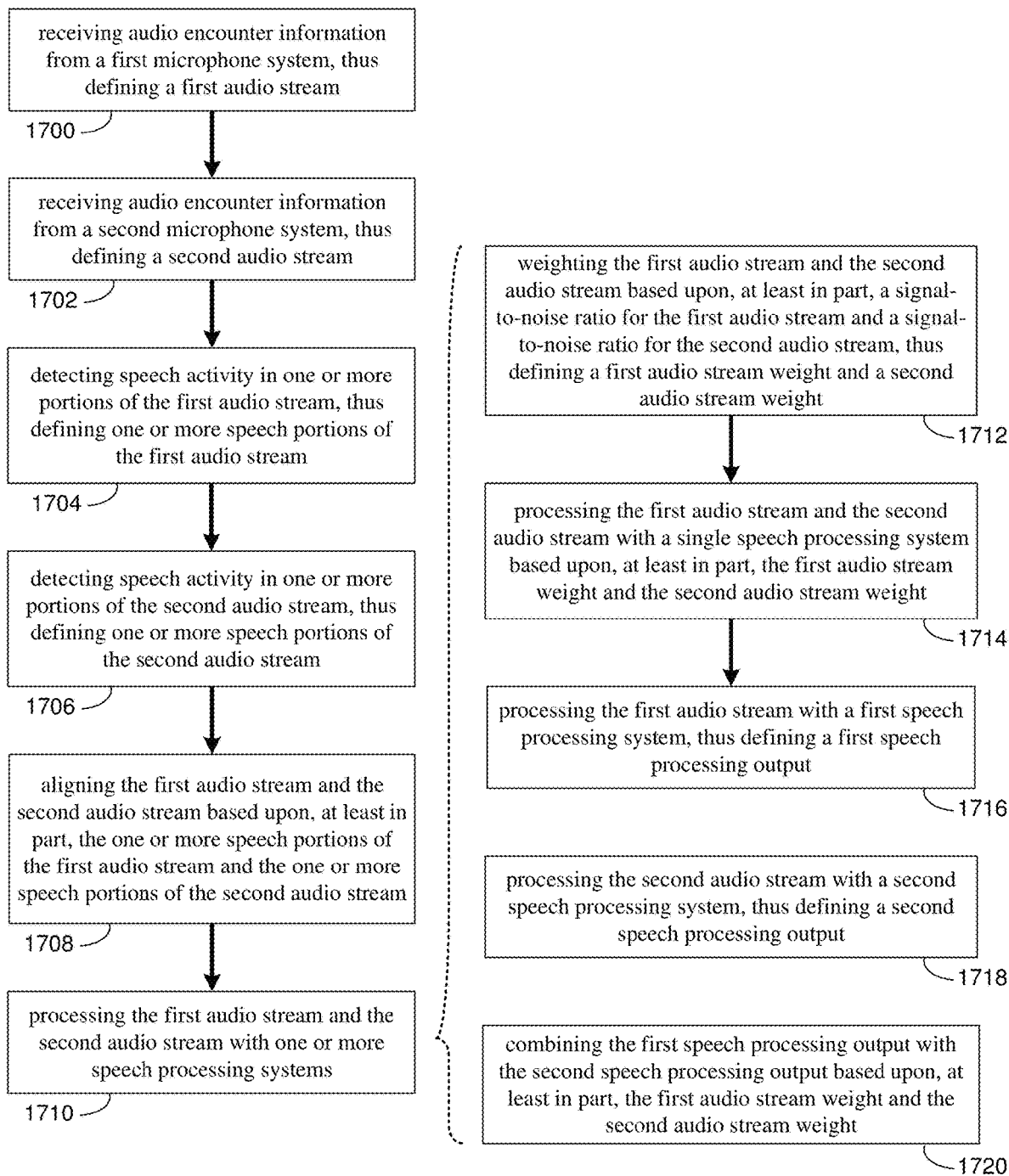
FIG. 17 is a flow chart of one implementation of the automated clinical documentation process of FIG. 1.

Referring also at least to FIGS. 15-16, automated clinical documentation process 10 may receive 1500 a plurality of predefined beams associated with a microphone array. A plurality of predefined nulls associated with the microphone array may be received 1502. One or more predefined beams from the plurality of predefined beams or one or more predefined nulls from the plurality of predefined nulls may be selected 1504. A microphone array may obtain 1506 audio encounter information, via the microphone array, using at least one of the one or more selected beams and the one or more selected nulls.

In some implementations, automated clinical documentation process 10 may receive 1500 a plurality of predefined beams associated with a microphone array. As discussed above, automated clinical documentation process 10 may predefine a plurality of predefined beams associated with a microphone array. For example, automated clinical documentation process 10 may predefine a plurality of beams based upon, at least in part, information associated with acoustic environment. As discussed above, a beam may generally include a pattern of constructive interference among microphones of a microphone array that is generated by modifying the phase and/or amplitude of the signal at each microphone of the microphone array. The pattern of constructive interference may improve the signal processing performance of the microphone array. In some implementations, automated clinical documentation process 10 may predefine the plurality of beams by adjusting the phase and/or amplitude of the signal at each microphone of the microphone array. In some implementations, automated clinical documentation process 10 may provide the predefined beams to beam and null selection module 408. In one example, automated clinical documentation process 10 may receive 1500 the plurality of predefined beams as a vector of phases and/or amplitudes for each signal of each microphone channel of the microphone array to achieve a desired sensitivity pattern. In another example and as discussed above, automated clinical documentation process 10 may receive 1500 the plurality of predefined beams as a plurality of predefined filters that produce the plurality of predefined beams.

In some implementations, the plurality of predefined beams may include one or more predefined beams configured to receive audio encounter information from one or more target speaker locations within an acoustic environment. For example and as discussed above, automated clinical documentation process 10 may receive information associated with an acoustic environment. In some implementations, the acoustic environment information may indicate one or more target speaker locations where a speaker is likely to speak from within the acoustic environment. Accordingly, automated clinical documentation process 10 may receive 1500 predefined beams configured to receive audio encounter information from the one or more target speaker locations within the acoustic environment.

For example and referring again to FIG. 6, automated clinical documentation process 10 may receive 1500 a plurality of predefined beams configured to receive audio encounter information from the one or more target speaker locations within the acoustic environment. Suppose that automated clinical documentation process 10 determines from the information associated with acoustic environment 600, that a patient is most likely to speak while sitting on or near the examination table at approximately 45° from the base of microphone array 200; a doctor is most likely to speak while sitting on or near the desk at approximately 90° from the base of microphone array 200; and that other patients or other third parties are most likely to speak from at approximately 120° from the base of microphone array 200. In this example, automated clinical documentation process 10 may receive 1500 predefined beam 220 configured for receiving audio encounter information from a patient (e.g., encounter participant 228); beam 222 configured for receiving audio encounter information from a doctor (e.g., encounter participant 226); and beam 224 configured for receiving audio encounter information from another patient/third party (e.g., encounter participant 230).

In some implementations, automated clinical documentation process 10 may receive 1502 a plurality of predefined nulls associated with the microphone array. As discussed above, a null may generally include a pattern of destructive interference among microphones of a microphone array that is generated by modifying the phase and/or amplitude of the signal at each microphone of the microphone array. The pattern of destructive interference may limit the reception of signals by the microphone array. In some implementations, automated clinical documentation process 10 may predefine the plurality of nulls by adjusting the phase and/or amplitude of the signal at each microphone of the microphone array via a plurality of filters (e.g., a plurality of FIR filters). In one example, automated clinical documentation process 10 may receive 1502 the plurality of predefined nulls as a vector of phases and/or amplitudes for each signal of each microphone channel of the microphone array to achieve a desired sensitivity pattern. In another example and as discussed above, automated clinical documentation process 10 may receive 1502 the plurality of predefined nulls as a plurality of predefined filters that produce the plurality of predefined nulls.

In some implementations, the plurality of predefined nulls may include one or more predefined nulls configured to limit receiving audio encounter information from one or more target speaker locations within an acoustic environment. For example and as discussed above, automated clinical documentation process 10 may receive information associated with an acoustic environment. In some implementations, the acoustic environment information may indicate one or more target speaker locations where a speaker is likely to speak from within the acoustic environment. Accordingly, automated clinical documentation process 10 may receive 1502 predefined beams configured to limit receiving audio encounter information from the one or more target speaker locations within the acoustic environment.

For example and referring again to FIG. 6, automated clinical documentation process 10 may receive 1502 a plurality of predefined nulls configured to receive audio encounter information from the one or more target speaker locations within the acoustic environment. Suppose that automated clinical documentation process 10 determines from the information associated with acoustic environment 600, that a patient is most likely to speak while sitting on or near the examination table at approximately 45° from the base of microphone array 200; a doctor is most likely to speak while sitting on or near the desk at approximately 90° from the base of microphone array 200; and that other patients or other third parties are most likely to speak from at approximately 120° from the base of microphone array 200. In this example and referring also to FIG. 7, automated clinical documentation process 10 may predefine null 252 to limit receiving audio encounter information from a patient (e.g., encounter participant 228); null 254 to limit receiving audio encounter information from a doctor (e.g., encounter participant 226); and null 256 to limit receiving audio encounter information from another patient/third party (e.g., encounter participant 230).

In some implementations, automated clinical documentation process 10 may select 1504 at least one of: one or more predefined beams from the plurality of predefined beams, thus defining one or more selected beams; and one or more predefined nulls from the plurality of predefined nulls, thus defining one or more selected nulls. Selecting a predefined beam and/or a predefined null may include selecting a pattern or combination of predefined beams and/or predefined nulls to achieve a particular microphone array sensitivity. For example and as will be described in greater detail below, suppose automated clinical documentation process 10 determines that the doctor (e.g., encounter participant 226) is speaking. In this example, automated clinical documentation process 10 may select 1504 one or more beams and/or nulls to achieve a beamforming pattern that enables microphone array 200 to receive audio encounter information from doctor (e.g., encounter participant 226). In some implementations, the one or more selected beams may enable audio encounter information to be received from doctor (e.g., encounter participant 226) and the one or more selected nulls may limit the reception of audio encounter information from other speakers or noise sources.

In some implementations, automated clinical documentation process 10 may receive 1508 speaker metadata associated with one or more portions of audio encounter information. For example and as discussed above, automated clinical documentation process 10 may, for each portion of audio encounter information 106, generate a "label" or speaker metadata with the speaker representation and speaker location information associated with that portion of the audio encounter information. As discussed above, a speaker representation may include a cluster of data associated with a unique speaker within an acoustic environment and the speaker location information may include information indicating the location of the speaker within the acoustic environment. In some implementations, automated clinical documentation process 10 may utilize the speaker representation and speaker location information to select particular beams and/or nulls for beamforming via a microphone array.

In some implementations, selecting 1504 at least one of the one or more beams and the one or more nulls may include selecting 1510 at least one of the one or more beams and the one or more nulls based upon, at least in part, the speaker metadata associated with the one or more portions of the audio encounter information. For example, automated clinical documentation process 10 may determine a speaker location within the acoustic environment and a speaker identity from the speaker metadata. In one instance, suppose that speaker metadata 1400 indicates that the doctor (e.g., encounter participant 226) is speaking (e.g., based upon, at least in part, speaker metadata including a speaker identity associated with the doctor (e.g., encounter participant 226) and speaker location information indicating that audio encounter information is being received from near the doctor's desk). In this example, automated clinical documentation process 10 may select one or more beams and/or one or more nulls based upon, at least in part, the speaker metadata indicating that the doctor (e.g., encounter participant 226) is speaking.

In some implementations, selecting 1510 at least one of the one or more beams and the one or more nulls based upon, at least in part, the speaker metadata associated with the one or more portions of the audio encounter information may include selecting 1512 the one or more predefined beams configured to receive audio encounter information from the one or more target speaker locations within the acoustic environment based upon, at least in part, the speaker metadata associated with the one or more portions of the audio encounter information. Continuing with the above example where speaker metadata 1400 indicates that the doctor (e.g., encounter participant 226) is speaking, automated clinical documentation process 10 may determine which beam(s) provide microphone sensitivity for the speaker location included in speaker metadata 1400. For example, suppose automated clinical documentation process 10 determines that beam 222 (as shown in FIG. 6) provides microphone sensitivity at or adjacent to the speaker location included in speaker metadata 1400. In this example, automated clinical documentation process 10 may select 1512 beam 222 for receiving audio encounter information from the doctor (e.g., encounter participant 226). While an example of selecting a single beam has been provided, it will be appreciated that any number of beams may be selected within the scope of the present disclosure.

In some implementations, selecting 1504 at least one of the one or more beams and the one or more nulls based upon, at least in part, the speaker metadata associated with the one or more portions of the audio encounter information may include selecting 1514 the one or more predefined nulls configured to limit receiving audio encounter information from the one or more target speaker locations within the acoustic environment based upon, at least in part, the speaker metadata associated with the one or more portions of the audio encounter information. Continuing with the above example where speaker metadata 1400 indicates that the doctor (e.g., encounter participant 226) is speaking, automated clinical documentation process 10 may determine which null(s) limit microphone sensitivity for other speaker locations and/or noise sources included in speaker metadata 1400. For example, suppose automated clinical documentation process 10 determines that null 252 (as shown in FIG. 7) limits microphone sensitivity at or adjacent to a speaker location associated with encounter participant 228 and that null 256 (as shown in FIG. 7) limits microphone sensitivity at or adjacent to a speaker location associated with encounter participants 230, 242.

In addition, suppose that automated clinical documentation process 10 determines that null 248 limits microphone sensitivity at or adjacent to a first noise source (e.g., fan 244) and that null 250 limits microphone sensitivity at or adjacent to a second noise source (e.g., doorway 246). In this example, automated clinical documentation process 10 may select 1514 nulls 248, 250, 252, 254 to limit receiving audio encounter information from other encounter participants and noise sources. While an example of selecting four nulls has been provided, it will be appreciated that any number of nulls may be selected within the scope of the present disclosure.

In some implementations, automated clinical documentation process 10 may select 1504 at least one of the one or more beams and the one or more nulls based upon, at least in part, the information associated with the acoustic environment. As discussed above and in some implementations, automated clinical documentation process 10 may receive information associated with the acoustic environment. In some implementations, automated clinical documentation process 10 may select particular beams and/or nulls to use when obtaining 1506 audio encounter information with a microphone array based upon, at least in part, the acoustic properties of the acoustic environment. For example, suppose the acoustic environment information indicates that acoustic environment 600 includes a particular reverberation level. In this example, automated clinical documentation process 10 may select particular beams and/or nulls to account for and/or to minimize signal degradation associated with the reverberation level of acoustic environment 600. Accordingly, automated clinical documentation process 10 may dynamically select beams and/or nulls based upon, at least in part, various acoustic properties of the acoustic environment.

In some implementations, automated clinical documentation process 10 may obtain 1506 audio encounter information, via the microphone array, using at least one of the one or more selected beams and the one or more selected nulls. In some implementations, automated clinical documentation process 10 may utilize the predefined plurality of beams and plurality of nulls to obtain 1506 audio encounter information from particular speakers and to limit receiving audio encounter information from other speakers. Continuing with the above example and as shown in FIG. 16, automated clinical documentation process 10 may obtain 1506 audio encounter information 106A from the doctor (e.g., encounter participant 226) via microphone array 200 with the one or more selected beams (e.g., beam 222) and the one or more nulls (e.g., nulls 248, 250, 252, 254).

In some implementations and referring again to FIG. 4, automated clinical documentation process 10 may provide the audio encounter information obtained 1506 with the selected beams and/or selected nulls to a device selection and weighting module (e.g., device selection and weighting module 410). As will be discussed in greater detail below, automated clinical documentation process 10 may provide audio encounter information received from the microphone array (e.g., a first microphone system) to device selection and weighting module 410 to determine which audio stream (i.e., stream of audio encounter information) to process with a speech processing system (e.g., speech processing system 418). As will be discussed in greater detail below, device selection and weighting module may select from a plurality of audio streams (e.g., an audio stream from the first microphone system and an audio stream from a second microphone system). In this manner, automated clinical documentation process 10 may select an audio stream (or from portions of an audio stream) from the plurality of audio streams to provide to a speech processing system.

Referring also at least to FIGS. 17-20B, automated clinical documentation process 10 may receive 1700 audio encounter information from a first microphone system, thus defining a first audio stream. Audio encounter information may be received 1702 from a second microphone system, thus defining a second audio stream. Speech activity may be detected 1704 in one or more portions of the first audio stream, thus defining one or more speech portions of the first audio stream. Speech activity may be detected 1706 in one or more portions of the second audio stream, thus defining one or more speech portions of the second audio stream. The first audio stream and the second audio stream may be aligned 1708 based upon, at least in part, the one or more speech portions of the first audio stream and the one or more speech portions of the second audio stream.

Figure 18:
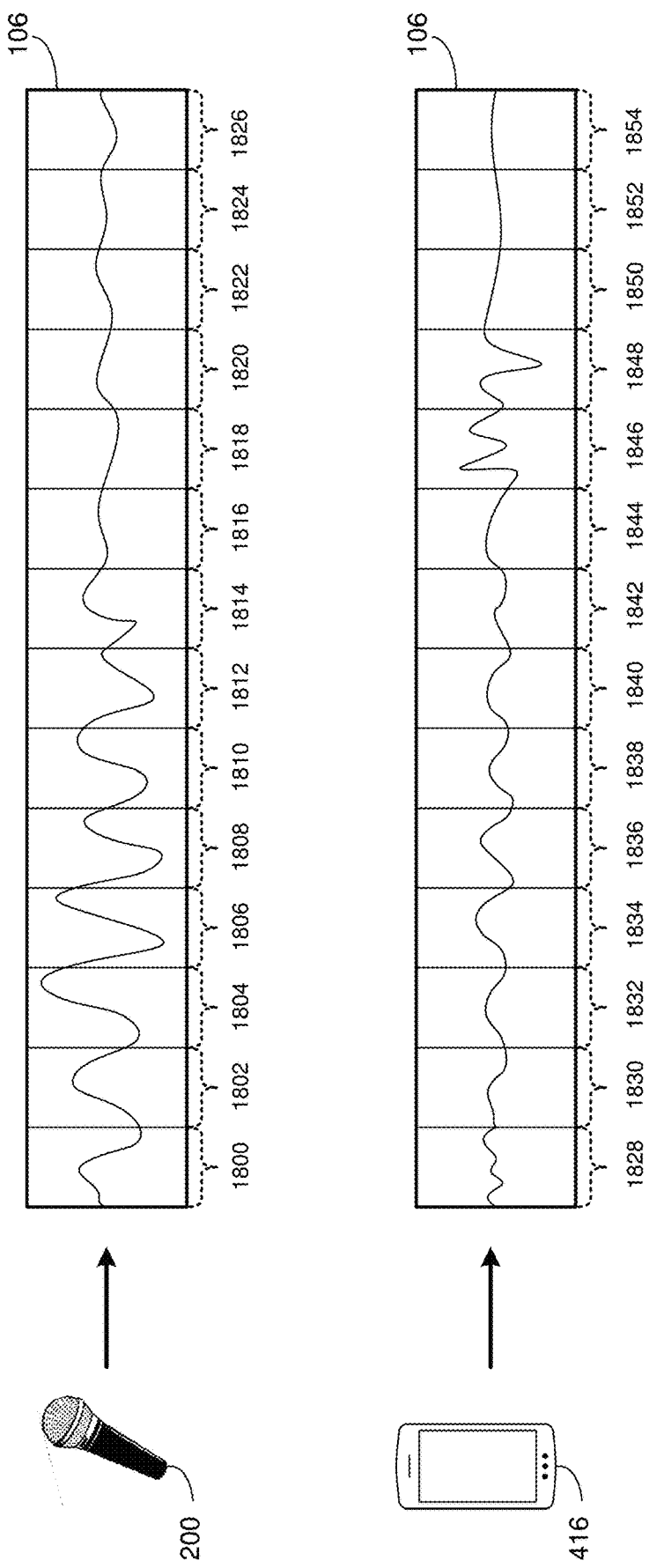
FIGS. 18-19 are diagrammatic views of the alignment of audio encounter information received by various microphone systems according to various implementations of the automated clinical documentation process of FIG. 1.

In some implementations, automated clinical documentation process 10 may receive 1700 audio encounter information from a first microphone system, thus defining a first audio stream. As discussed above and in some implementations, the first microphone system may be a microphone array. For example and as shown in FIG. 4, automated clinical documentation process 10 may receive audio encounter information (e.g., audio encounter information 106) from a first microphone system (e.g., microphone array 200 with audio acquisition devices 202, 204, 206, 208, 210, 212, 214, 216, 218). Referring again to FIG. 6, audio encounter information 106 may be received 1700 with one or more beams and/or one or more nulls generated by microphone array 200. As shown in FIG. 4, the solid lines between beam and null selection module 408 and device selection and weighting module 410; and between beam and null selection module 408 and alignment module 412 may represent first audio stream received from microphone array 200. Referring also to FIG. 18 and in some implementations, automated clinical documentation process 10 may receive audio encounter information with one or more portions (e.g., portions 1800, 1802, 1804, 1806, 1808, 1810, 1812, 1814, 1816, 1818, 1820, 1822, 1824, 1826) from a first microphone system (e.g., microphone array 200), thus defining a first audio stream.

In some implementations, automated clinical documentation process 10 may receive 1702 audio encounter information from a second microphone system, thus defining a second audio stream. In some implementations, the second microphone system may be a mobile electronic device. For example and as shown in FIG. 4, automated clinical documentation process 10 may receive audio encounter information from a second microphone system (e.g., mobile electronic device 416). As shown in FIG. 4, the lines with dashes and dots between mobile electronic device 516 and VAD module 414; between VAD module 414 and alignment module 412; and between alignment module 412 and device selection and weighting module 410 may represent first audio stream received from microphone array 200. Referring again to FIG. 18 and in some implementations, automated clinical documentation process 10 may receive audio encounter information with one or more portions (e.g., portions 1828, 1830, 1832, 1834, 1836, 1838, 1840, 1842, 1844, 1846, 1848, 1850, 1852, 1854) from a second microphone system (e.g., mobile electronic device 416), thus defining a second audio stream.

In some implementations, automated clinical documentation process 10 may detect 1704 speech activity in one or more portions of the first audio stream, thus defining one or more speech portions of the first audio stream. As discussed above and in some implementations, automated clinical documentation process 10 may identify speech activity within one or more portions of the audio encounter information based upon, at least in part, a correlation among the audio encounter information received from the microphone array. Referring also to the example of FIG. 9 and in some implementations, audio encounter information 106 may include a plurality of portions or frames of audio information. In some implementations, automated clinical documentation process 10 may determine a correlation among the audio encounter information received from microphone array 200. For example, automated clinical documentation process 10 may compare the one or more portions of audio encounter information 106 to determine a degree of correlation between the audio encounter information present in each portion across the plurality of microphones of the microphone array. In some implementations and as known in the art, automated clinical documentation process 10 may perform various cross-correlation processes to determine a degree of similarity between the one or more portions of audio encounter information 106 across the plurality of microphones of microphone array 200.

For example, suppose automated clinical documentation process 10 receives just ambient noise (i.e., no speech and no directional noise sources). Automated clinical documentation process 10 may determine that the spectrum observed in each microphone channel will be different (i.e. uncorrelated at each microphone). However, suppose automated clinical documentation process 10 receives a speech or other 'directional' signal within audio encounter information. In this example, automated clinical documentation process 10 may determine that one or more portions of the audio encounter information (e.g., the portions of audio encounter information with speech components) are highly correlated at each microphone in the microphone array.

In some implementations, automated clinical documentation process 10 may identify speech activity within one or more portions of the audio encounter information based upon, at least in part, determining a threshold amount or degree of correlation among the audio encounter information received from the microphone array. For example and as discussed above, various thresholds may be defined (e.g., user-defined, default thresholds, automatically defined via automated clinical documentation process 10, etc.) to determine when portions of audio encounter information are sufficiently correlated. Accordingly, in response to determining at least a threshold degree of correlation among the portions of audio encounter information across the plurality of microphones, automated clinical documentation process 10 may determine or identify speech activity within the one or more portions of the audio encounter information. In combination with determining a threshold correlation among the portions of audio encounter information, automated clinical documentation process 10 may identify speech activity using other approaches known in the art for voice activity detection (VAD) such as filtering, noise reduction, the application of classification rules, etc. In this manner, conventional VAD techniques may be used in combination with the determination of a threshold correlation among the one or more portions of the audio encounter information to identify speech activity within the one or more portions of the audio encounter information. Referring again to FIG. 18, automated clinical documentation process 10 may detect speech activity in portions 1800, 1802, 1804, 1806, 1808, 1810, 1812.

In some implementations, automated clinical documentation process 10 may detect 1706 speech activity in one or more portions of the second audio stream, thus defining one or more speech portions of the second audio stream. For example and in some implementations, automated clinical documentation process 10 may perform various known voice activity detection (VAD) processes to determine which portions of audio encounter information received by mobile electronic device 416 include speech activity. In this manner, automated clinical documentation process 10 may detect 1706 speech activity in the one or more portions of the second audio stream. Referring again to FIG. 18, automated clinical documentation process 10 may detect speech activity in portions 1830, 1832, 1834, 1836, 1838, 1840, 1842 using various known VAD processes.

Figure 19:
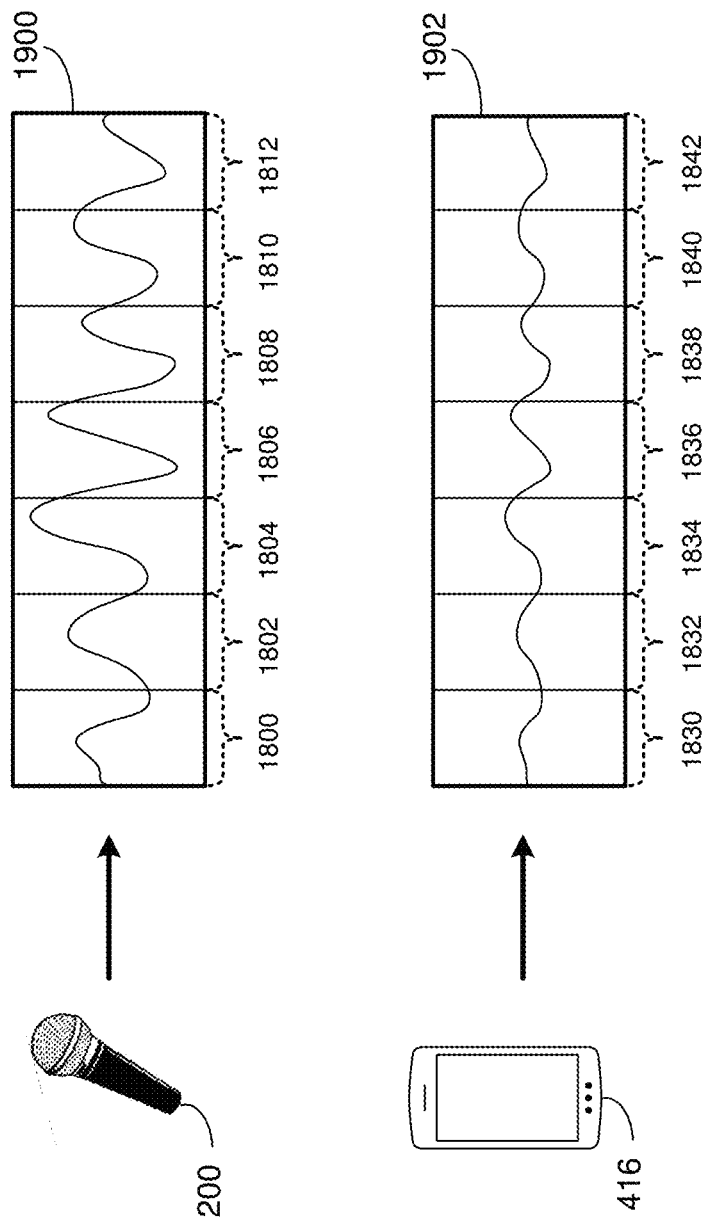

In some implementations, automated clinical documentation process 10 may align 1708 the first audio stream and the second audio stream based upon, at least in part, the one or more speech portions of the first audio stream and the one or more speech portions of the second audio stream. In some implementations, automated clinical documentation process 10 may utilize an echo cancellation-based adaptive filtering approach where the delay between the first audio stream and the second audio stream is estimated from a filter bulk delay and the sparseness of the filter is used to ensure that the two audio streams can be aligned. Referring also to FIG. 19 and in some implementations, automated clinical documentation process 10 may align first audio stream 1900 and second audio stream 1902 based upon, at least in part, the one or more speech portions of the first audio stream (e.g., speech portions 1800, 1802, 1804, 1806, 1808, 1810, 1812 of first audio stream 1900) and the one or more speech portions of the second audio stream (e.g., speech portions 1830, 1832, 1834, 1836, 1838, 1840, 1842 of second audio stream 1902). In the example of FIG. 19, while each audio stream may have different amplitude values at a given point in time, the first and second audio streams may be temporally-aligned.

In some implementations and in response to aligning the first audio stream and the second audio stream, automated clinical documentation process 10 may process 1710 the first audio stream and the second audio stream with one or more speech processing systems. Referring also to FIGS. 20A-20B, automated clinical documentation process 10 may provide the first audio stream and the second audio stream from the device selection and weighting module (e.g., device selection and weighting module 410) to one or more speech processing systems (e.g., speech processing system 418, 2000, 2002). Examples of speech processing systems may generally include automated speech recognition (ASR) systems, voice biometric systems, emotion detection systems, medical symptom detection systems, hearing enhancement systems, etc. As will be discussed in greater detail below, because different portions of the audio stream may be processed more accurately by the one or more speech processing systems based upon, at least in part, the signal quality of each audio stream. Accordingly, automated clinical documentation process 10 may selectively process 1701 particular portions from each audio stream with the one or more speech processing systems.

In some implementations, processing 1710 the first audio stream and the second audio stream with one or more speech processing systems may include weighting 1712 the first audio stream and the second audio stream based upon, at least in part, a signal-to-noise ratio for the first audio stream and a signal-to-noise ratio for the second audio stream, thus defining a first audio stream weight and a second audio stream weight. In some implementations, device selection and weighting module 410 may be a machine learning system or model (e.g., a neural network-based model) configured to be trained to weight each audio stream such that the estimated speech processing system performance is maximized. For example, automated clinical documentation process 10 may train the device selection and weighting model based upon, at least in part, the signal-to-noise (SNR) ratio for each portion or frame of each audio stream. In some implementations and as will be discussed in greater detail below, the machine learning model of the device selection and weighting module may be trained jointly in an end-to-end manner to weight and select particular portions of the audio stream for processing with one or more speech processing systems.

Referring again to the example of FIG. 6, suppose a doctor (e.g., doctor 226) has mobile electronic device 416 near them as they are speaking to a patient (e.g., patient 228). In this example, a first microphone system (e.g., microphone array 200) and a second microphone system (e.g., mobile electronic device 416) may receive audio encounter information while the doctor (e.g., encounter participant 226) is speaking. As discussed above, automated clinical documentation process 10 may detect speech activity within each audio stream and may align the audio streams based upon, at least in part, the speech activity within each audio stream. Automated clinical documentation process 10 may weight 1712 each portion or frame of each audio stream based upon, at least in part, a SNR ratio for each audio stream. In this example, suppose the doctor (e.g., encounter participant 226) is speaking when near the doctor's desk. Suppose the doctor (e.g., encounter participant 226) moves quickly to the examination table to assist the patient (e.g., patient 228). During this period, the doctor (e.g., encounter participant 226) may be speaking. As such, while the doctor (e.g., encounter participant 226) may move outside of beam 222 towards null 248, microphone array 200 may receive lower quality audio encounter information than mobile electronic device 416 (i.e., the audio encounter information received by microphone array 200 may have a lower SNR ratio). Accordingly, automated clinical documentation process 10 may weight 1712 the portions of the audio encounter information received from microphone array 200 while the doctor is moving with a lower weight than the audio encounter information received from mobile electronic device 416. Additionally/alternatively, automated clinical documentation process 10 may weight 1712 the portions of audio encounter information received from mobile electronic device 416 while the doctor is moving with a higher weight than the audio encounter information received from microphone array 200. In this manner, automated clinical documentation process 10 may utilize the weighting of portions of each audio stream to automated clinical documentation process 101 each audio stream with one or more speech processing systems.

In some implementations, processing 1710 the first audio stream and the second audio stream with one or more speech processing systems may include processing 1714 the first audio stream and the second audio stream with a single speech processing system based upon, at least in part, the first audio stream weight and the second audio stream weight. Referring again to FIG. 20A and in some implementations, automated clinical documentation process 10 may automated clinical documentation process 101 the first audio stream (e.g., represented as a solid line between device selection weighting module 410 and speech processing system 418) and the second audio stream (e.g., represented as a dashed and dotted line between device selection weighting module 410 and speech processing system 418) with a single speech processing system (e.g., speech processing system 418) based upon, at least in part, the first audio stream weight and the second audio stream weight (e.g., where both audio stream weights are represented as the dashed line between the device selection weighting module 410 and speech processing system 418). In some implementations, automated clinical documentation process 10 may, via speech processing system 418, select particular portions of either audio stream to process based upon, at least in part, the first audio stream weight and the second audio stream weight.

In some implementations, processing 1710 the first audio stream and the second audio stream with one or more speech processing systems may include processing 1716 the first audio stream with a first speech processing system, thus defining a first speech processing output; processing 1718 the second audio stream with a second speech processing system, thus defining a second speech processing output; and combining 1720 the first speech processing output with the second speech processing output based upon, at least in part, the first audio stream weight and the second audio stream weight. Referring again to FIG. 20B and in some implementations, automated clinical documentation process 10 may process 1716 the first audio stream (e.g., represented as a solid line between device selection weighting module 410 and speech processing system 418) with a first speech processing system to generate a first speech processing output (e.g., represented as a solid line between speech processing system 418 and speech processing system 2002). Automated clinical documentation process 10 may process 1718 the second audio stream (e.g., represented as a dashed and dotted line between device selection weighting module 410 and speech processing system 2000) with a second speech processing system (e.g., speech processing system 2000) to generate a second speech processing output (e.g., represented as a solid line between speech processing system 2000 and speech processing system 2002). In some implementations, automated clinical documentation process 10 may combine 1720, via a third speech processing system (e.g., speech processing system 2002), the first speech processing output with the second speech processing output based upon, at least in part, the first audio stream weight and the second audio stream weight (e.g., where both audio stream weights are represented as the dashed line between the device selection weighting module 410 and speech processing system 2002). In some implementations, automated clinical documentation process 10 may, via speech processing system 2002, select particular portions of either audio stream to process or output based upon, at least in part, the first audio stream weight and the second audio stream weight. While an example of e.g., two audio streams has been provided, it will be appreciated that any number of audio streams may be used within the scope of the present disclosure.

In some implementations, automated clinical documentation process 10 may generate an encounter transcript (e.g., encounter transcript 234) with output of the one or more speech processing systems, wherein at least a portion of the encounter transcript (e.g., encounter transcript 234) may be processed to populate at least a portion of a medical record (e.g., medical record 236) associated with the patient encounter (e.g., a visit to a doctor's office). For example, automated clinical documentation process 10 may utilize speaker representation to identify speakers in audio encounter information when generating the encounter transcript. For example, automated clinical documentation process 10 may generate a diarized encounter transcript (e.g., encounter transcript 234) that identifies the verbal comments and utterances made by particular speakers based upon, at least in part, the speaker representations defined for each encounter participant. In the above example, automated clinical documentation process 10 may generate diarized encounter transcript 234 with verbal comments and utterances may by "Doctor Susan Jones" (e.g., encounter participant 226), "Patient Paul Smith" (e.g., encounter participant 228), and "Unknown Participant" (e.g., encounter participant 230).

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   receiving a plurality of predefined beams associated with a microphone array wherein the plurality of predefined beams include one or more predefined beams configured to receive audio encounter information from one or more target speaker locations within an acoustic environment;
   receiving a plurality of predefined nulls associated with the microphone array wherein the plurality of predefined nulls include one or more predefined nulls configured to limit receiving the audio encounter information from the one or more target speaker locations within the acoustic environment;
   receiving speaker metadata associated with one or more portions of the audio encounter information;
   selecting:
      one or more predefined beams from the plurality of predefined beams, thus defining one or more selected beams; and one or more predefined nulls from the plurality of predefined nulls, thus defining one or more selected nulls, wherein selecting at least one of the one or more beams and the one or more nulls includes selecting at least one of the one or more beams and the one or more nulls based upon, at least in part, the speaker metadata associated with the one or more portions of the audio encounter information, and wherein selecting at least one of the one or more beams and the one or more nulls based upon, at least in part, the speaker metadata associated with the one or more portions of the audio encounter information includes selecting the one or more predefined nulls configured to limit receiving audio encounter information from the one or more target speaker locations within the acoustic environment based upon, at least in part, the speaker metadata associated with the one or more portions of the audio encounter information; and obtaining the audio encounter information, via the microphone array, using the one or more selected beams and the one or more selected nulls.

2. The computer-implemented method of claim 1, wherein selecting at least one of the one or more beams and the one or more nulls based upon, at least in part, the speaker metadata associated with the one or more portions of the audio encounter information includes selecting the one or more predefined beams configured to receive audio encounter information from the one or more target speaker locations within the acoustic environment based upon, at least in part, the speaker metadata associated with the one or more portions of the audio encounter information.

3. A computer program product residing on a non-transitory computer readable medium having a plurality of instructions stored thereon which, when executed by a processor, cause the processor to perform operations comprising:

receiving a plurality of predefined beams associated with a microphone array wherein the plurality of predefined beams include one or more predefined beams configured to receive audio encounter information from one or more target speaker locations within an acoustic environment;

receiving a plurality of predefined nulls associated with the microphone array wherein the plurality of predefined nulls include one or more predefined nulls configured to limit receiving the audio encounter information from the one or more target speaker locations within the acoustic environment;

receiving speaker metadata associated with one or more portions of the audio encounter information;

selecting:
one or more predefined beams from the plurality of predefined beams, thus defining one or more selected beams; and
one or more predefined nulls from the plurality of predefined nulls, thus defining one or more selected nulls, wherein selecting at least one of the one or more beams and the one or more nulls includes selecting at least one of the one or more beams and the one or more nulls based upon, at least in part, the speaker metadata associated with the one or more portions of the audio encounter information, and wherein selecting at least one of the one or more beams and the one or more nulls based upon, at least in part, the speaker metadata associated with the one or more portions of the audio encounter information includes selecting the one or more predefined nulls configured to limit receiving audio encounter information from the one or more target speaker locations within the acoustic environment based upon, at least in part, the speaker metadata associated with the one or more portions of the audio encounter information; and obtaining the audio encounter information, via the microphone array, using the one or more selected beams and the one or more selected nulls.

4. The computer program product of claim 3, wherein selecting at least one of the one or more beams and the one or more nulls based upon, at least in part, the speaker metadata associated with the one or more portions of the audio encounter information includes selecting the one or more predefined beams configured to receive audio encounter information from the one or more target speaker locations within the acoustic environment based upon, at least in part, the speaker metadata associated with the one or more portions of the audio encounter information.

5. A computing system comprising:
a memory; and
a processor configured to receive a plurality of predefined beams associated with a microphone array, wherein the plurality of predefined beams include one or more predefined beams configured to receive audio encounter information from one or more target speaker locations within an acoustic environment, wherein the processor is further configured to receive a plurality of predefined nulls associated with the microphone array, wherein the plurality of predefined nulls include one or more predefined nulls configured to limit receiving the audio encounter information from the one or more target speaker locations within the acoustic environment, wherein the processor is further configured to receive speaker metadata associated with one or more portions of the audio encounter information, wherein the processor is further configured to select: one or more predefined beams from the plurality of predefined beams, thus defining one or more selected beams and one or more predefined nulls from the plurality of predefined nulls, thus defining one or more selected nulls, wherein selecting at least one of the one or more beams and the one or more nulls includes selecting at least one of the one or more beams and the one or more nulls based upon, at least in part, the speaker metadata associated with the one or more portions of the audio encounter information, and wherein selecting at least one of the one or more beams and the one or more nulls based upon, at least in part, the speaker metadata associated with the one or more portions of the audio encounter information includes selecting the one or more predefined nulls configured to limit receiving audio encounter information from the one or more target speaker locations within the acoustic environment based upon, at least in part, the speaker metadata associated with the one or more portions of the audio encounter information, and wherein the processor is further configured to obtain the audio encounter information, via the microphone array, using the one or more selected beams and the one or more selected nulls.

6. The computing system of claim 5, wherein selecting at least one of the one or more beams and the one or more nulls based upon, at least in part, the speaker metadata associated with the one or more portions of the audio encounter information includes selecting the one or more predefined beams configured to receive audio encounter information from the one or more target speaker locations within the acoustic environment based upon, at least in part, the speaker metadata associated with the one or more portions of the audio encounter information.

\* \* \* \* \*